(12) United States Patent
Hildebrandt et al.

(10) Patent No.: US 9,914,959 B2
(45) Date of Patent: Mar. 13, 2018

(54) MULTIPLEXED HOMOGENEOUS OLIGONUCLEOTIDE DETECTION

(71) Applicants: UNIVERSITE PARIS-SUD, Orsay (FR); CENTRE NATIONAL DE LA RECHERCHE SCIENTIFIQUE, Paris (FR); LUMIPHORE INC., Berkeley, CA (US)

(72) Inventors: Niko Hildebrandt, Orsay (FR); Zongwen Jin, Shenzhen (CN)

(73) Assignees: UNIVERSITE PARIS-SUD, Orsay (FR); CENTRE NATIONAL DE LA RECHERCHE SCIENTIFIQUE, Paris (FR); LUMIPHORE INC., Berkeley, CA (US)

( * ) Notice: Subject to any disclaimer, the term of this patent is extended or adjusted under 35 U.S.C. 154(b) by 0 days.

(21) Appl. No.: 15/313,192

(22) PCT Filed: May 25, 2015

(86) PCT No.: PCT/EP2015/061487
§ 371 (c)(1),
(2) Date: Nov. 22, 2016

(87) PCT Pub. No.: WO2015/181101
PCT Pub. Date: Dec. 3, 2015

(65) Prior Publication Data
US 2017/0152551 A1 Jun. 1, 2017

(30) Foreign Application Priority Data
May 27, 2014 (EP) ..................... 14305794

(51) Int. Cl.
*C12Q 1/68* (2006.01)
*C07H 21/00* (2006.01)
*G01N 21/64* (2006.01)

(52) U.S. Cl.
CPC ....... *C12Q 1/6818* (2013.01); *G01N 21/6428* (2013.01); *G01N 2021/6439* (2013.01)

(58) Field of Classification Search
CPC .................................. C07H 21/00; C12Q 1/68
See application file for complete search history.

(56) References Cited

U.S. PATENT DOCUMENTS

| 4,868,103 A * | 9/1989 | Stavrianopoulos | C12Q 1/6818 435/5 |
| 4,988,617 A * | 1/1991 | Landegren | C12Q 1/6827 435/6.11 |
| 2003/0129611 A1* | 7/2003 | Bao | C12Q 1/6818 435/6.11 |
| 2006/0211000 A1 | 9/2006 | Sorge et al. | |
| 2008/0124810 A1 | 5/2008 | Terbrueggen | |
| 2008/0166707 A1 | 7/2008 | Han | |
| 2010/0167293 A1 | 7/2010 | Vann et al. | |
| 2011/0033855 A1 | 2/2011 | Hori et al. | |
| 2011/0124518 A1 | 5/2011 | Cantor | |
| 2011/0136116 A1 | 6/2011 | Barany et al. | |
| 2012/0282611 A1* | 11/2012 | Wangh | C12Q 1/6827 435/6.11 |
| 2014/0057263 A1* | 2/2014 | Engel | C12Q 1/6832 435/6.11 |
| 2014/0178878 A1* | 6/2014 | Muller | C12Q 1/6813 435/6.11 |
| 2014/0323354 A1* | 10/2014 | Paul | C12Q 1/6806 506/16 |

FOREIGN PATENT DOCUMENTS

WO 00/04192 A1 1/2000

OTHER PUBLICATIONS

Jin et al., Semiconductor quantum dots for in vitro diagnostics and cellular imaging. Trens in Biotechnology 30(7) :394(Jul. 2012).*
Jin et al., A Rapid, Amplification-Free, and Sensitive Diagnostic Assay for Single-Step Multiplexed Fluorescence Detection of miRNA. Angew. Chem. Int. Ed. 54: 10024 (2015).*
European Search Report from European Application No. 14305794. 1, dated Oct. 22, 2014.
International Search Report from International Patent Application No. PCT/EP2015/061487, dated Sep. 11, 2015.
Written Opinion from International Patent Application No. PCT/EP2015/061487, dated Sep. 11, 2015.
Abell, et al. "Label-Free Detection of Micro-RNA Hybridization Using Surface-Enhanced Raman Spectroscopy and Least-Squares Analysis" Journal of the American Chemical Society Jul. 12, 2012, v 134, p. 12889-12892.
Sipova, et al. "Surface Plasmon Resonance Biosensor for Rapid Label-Free Detection of MicroRNA at Subfemtomole Level" Anal Chem. Dec. 15, 2010, v 82, n 24, p. 10110-10115.
Le at al. "Ultrathin and smooth poly(methyl methacrylate) (PMMA) films for label-free biomolecule detection with total internal reflection ellipsometry (TIRE)" Biosensors and Bioelectronics, 2012, v 36, p. 250-256.
Chen et al. "A method of layer-by-layer gold nanoparticle hybridization in a quartz crystal microbalance DNA sensing system used to detect dengue virus" Nanotechnology, 2009, v 20, p. 1-10.
Zhang et al. "Label-free direct detection of MiRNAs with silicon nanowire biosensors" Biosensors and Bioelectronics, 2009, v 24, p. 2504-2508.
Jain et al. "Integration of Solid-State Nanopores in Microfluidic Networks via Transfer Printing of Suspended Membranes" Analytical Chemistry, Jan. 24, 2013, v 85, p. 3871-3878.

(Continued)

*Primary Examiner* — Ethan C Whisenant
(74) *Attorney, Agent, or Firm* — Greer, Burns & Crain, Ltd.

(57) ABSTRACT

A new kit is provided for detecting or quantifying the amount of one or multiple nucleic acid targets in a biological sample, and a detection or quantification method using this kit. The present kit is constituted by a universal energy donor probe, a universal energy acceptor probe and a couple of adaptors.

20 Claims, 14 Drawing Sheets

(56) References Cited

OTHER PUBLICATIONS

Kulkarni "Digital Multiplexed Gene Expression Analysis Using the NanoString nCounter System" Current Protocols in Molecular Biology, Apr. 2011, Wiley Online Library, p. 25B.10.1-25B.10.17.

De Planell-Saguer et al. "Analytical aspects of microRNA in diagnostics: A review" Analytica Chimica Acta, 2011, v 699, p. 134-152.

Gao et al. "A Label-Free Biosensor for Electrochemical Detection of Femtomolar MicroRNAs" Analytical Chemistry, 2013, v 85, p. 1624-1630.

Hildebrandt, "How to Apply FRET: From Experimental Design to Data Analysis" Förster Resonance Energy Transfer: From Theory to Applications, First Edition. 2014, p. 105-163.

Hotzer et al. "Fluorescence in Nanobiotechnology: Sophisticated Fluorophores for Novel Applications" www.small-journal.com, 2012, v 8, n 15, p. 2297-2326.

Fu et al. "Semiconductor Quantum Rods as Single Molecule Fluorescent Biological Labels" Nano Lett. Jan. 2007, v 7, n 1, 179-182.

Geibler et al. "Six-Color Time-Resolved Förster Resonance Energy Transfer for Ultrasensitive Multiplexed Biosensing" Journal of the American Chemical Society, 2013, v 135, p. 1102-1109.

\* cited by examiner

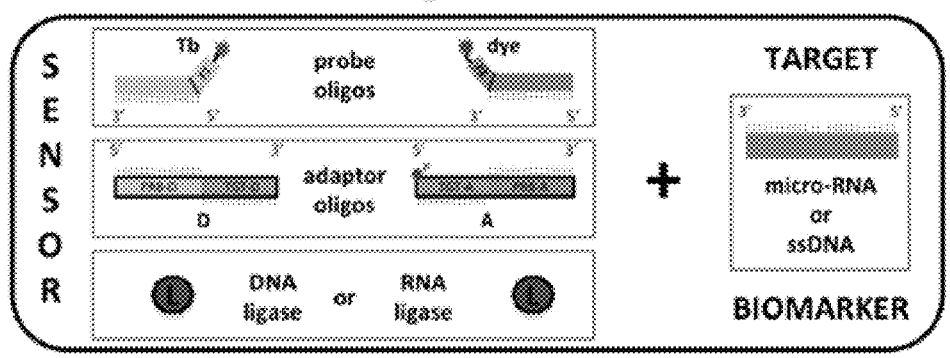
Figure 1a
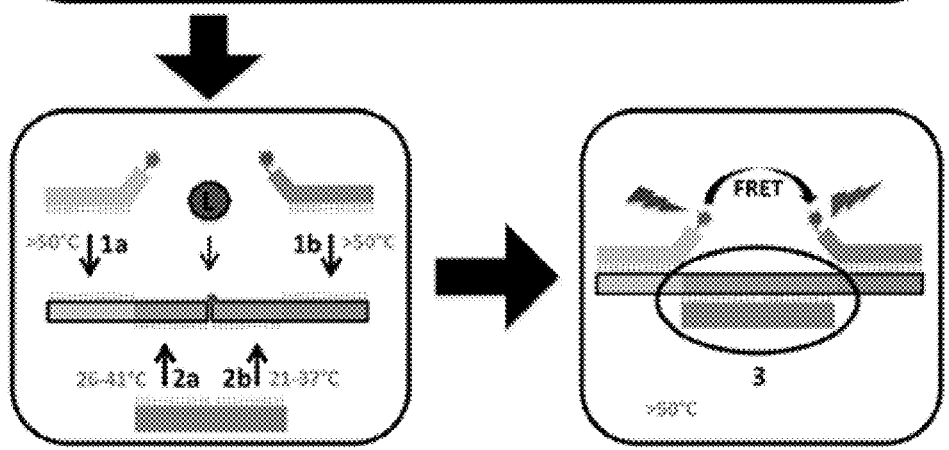
Figure 1b
Figure 1c
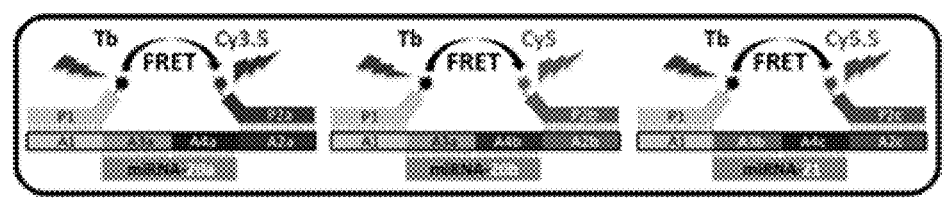
Figure 1d
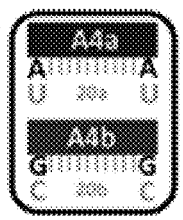
Figure 1e

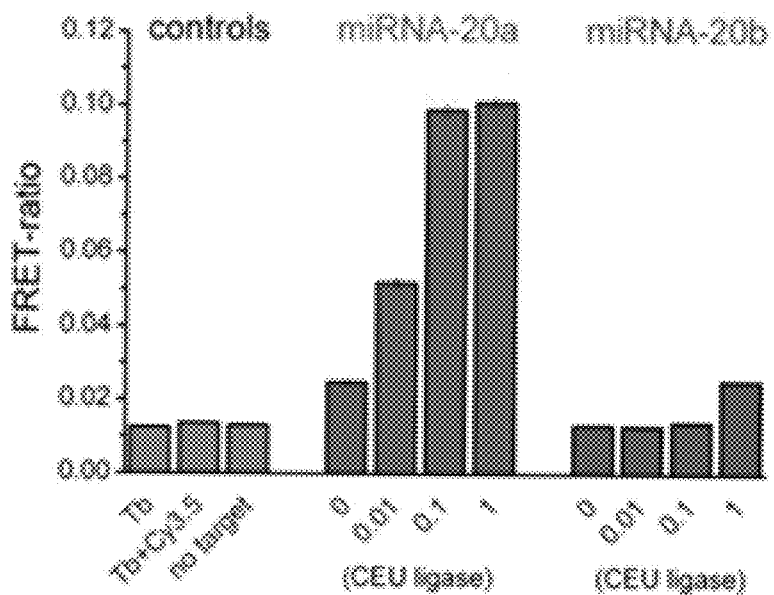
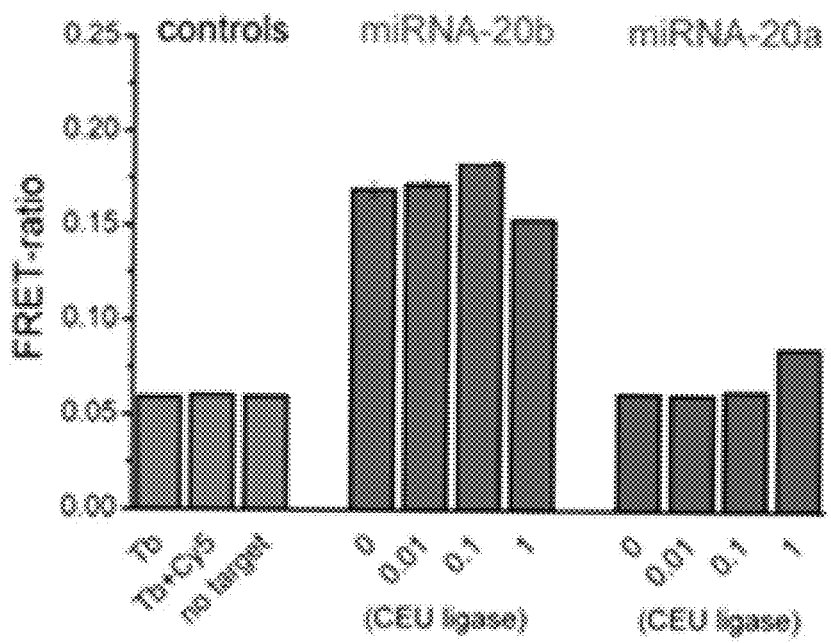

```
                         SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Probe

<400> SEQUENCE: 1
cgatcagtca ggcaaagcgg                                               20

<210> SEQ ID NO 2
<211> LENGTH: 21
<212> TYPE: DNA
<213> ORGANISM: Artificial Sequence
<220> FEATURE:
<223> OTHER INFORMATION: Probe

<400> SEQUENCE: 2
aaaaaacgat cagtcaggca a                                             21

<210> SEQ ID NO 3
<211> LENGTH: 23
<212> TYPE: DNA
<213> ORGANISM: artificial sequence
<220> FEATURE:
<223> OTHER INFORMATION: Probe

<400> SEQUENCE: 3
ttactgtgca cagaggaaaa aaa                                           23

<210> SEQ ID NO 4
<211> LENGTH: 23
<212> TYPE: DNA
<213> ORGANISM: artificial sequence
<220> FEATURE:
<223> OTHER INFORMATION: Probe

<400> SEQUENCE: 4
ttgtgttccg ataggctaaa aaa                                           23

<210> SEQ ID NO 5
<211> LENGTH: 23
<212> TYPE: DNA
<213> ORGANISM: artificial sequence
<220> FEATURE:
<223> OTHER INFORMATION: Probe

<400> SEQUENCE: 5
aatcaaggta acggactaaa aaa                                           23

<210> SEQ ID NO 6
<211> LENGTH: 33
<212> TYPE: DNA
<213> ORGANISM: artificial sequence
<220> FEATURE:
<223> OTHER INFORMATION: Adaptor

<400> SEQUENCE: 6
```

```
ccgctttgcc tgactgatcg ctacctgcac tat                                    33

<210> SEQ ID NO 7
<211> LENGTH: 32
<212> TYPE: DNA
<213> ORGANISM: artificial sequence
<220> FEATURE:
<223> OTHER INFORMATION: Adaptor

<400> SEQUENCE: 7
ccgctttgcc tgactgatcg ucaacaucag uc                                     32

<210> SEQ ID NO 8
<211> LENGTH: 32
<212> TYPE: DNA
<213> ORGANISM: artificial sequence
<220> FEATURE:
<223> OTHER INFORMATION: Adaptor

<400> SEQUENCE: 8
ccgctttgcc tgactgatcg tcaacatcag tc                                     32

<210> SEQ ID NO 9
<211> LENGTH: 40
<212> TYPE: DNA
<213> ORGANISM: artificial sequence
<220> FEATURE:
<223> OTHER INFORMATION: Adaptor

<400> SEQUENCE: 9
aagcacuuua tcctctgtgc acagtaaccc ctaaccctct                             40

<210> SEQ ID NO 10
<211> LENGTH: 40
<212> TYPE: DNA
<213> ORGANISM: artificial sequence
<220> FEATURE:
<223> OTHER INFORMATION: Adaptor

<400> SEQUENCE: 10
gagcacuuug agcctatcgg aacacaaccc ctaaccctct                             40

<210> SEQ ID NO 11
<211> LENGTH: 40
<212> TYPE: DNA
<213> ORGANISM: artificial sequence
<220> FEATURE:
<223> OTHER INFORMATION: Adaptor

<400> SEQUENCE: 11
ugauaagcua agtccgttac cttgattccc ctaaccctct                             40

<210> SEQ ID NO 12
<211> LENGTH: 40
<212> TYPE: DNA
<213> ORGANISM: artificial sequence
<220> FEATURE:
<223> OTHER INFORMATION: Adaptor

<400> SEQUENCE: 12
aagcacttta tcctctgtgc acagtaaccc ctaaccctct                             40

<210> SEQ ID NO 13
<211> LENGTH: 40
<212> TYPE: DNA
```

```
<213> ORGANISM: artificial sequence
<220> FEATURE:
<223> OTHER INFORMATION: Adaptor

<400> SEQUENCE: 13
gagcactttg agcctatcgg aacacaaccc ctaaccctct                              40

<210> SEQ ID NO 14
<211> LENGTH: 40
<212> TYPE: DNA
<213> ORGANISM: artificial sequence
<220> FEATURE:
<223> OTHER INFORMATION: Adaptor

<400> SEQUENCE: 14
tgataagcta agtccgttac cttgattccc ctaaccctct                              40

<210> SEQ ID NO 15
<211> LENGTH: 23
<212> TYPE: RNA
<213> ORGANISM: Homo sapiens

<400> SEQUENCE: 15
uaaagugcuu auagugcagg uag                                                23

<210> SEQ ID NO 16
<211> LENGTH: 23
<212> TYPE: RNA
<213> ORGANISM: Homo sapiens

<400> SEQUENCE: 16
caaagugcuc auagugcagg uag                                                23

<210> SEQ ID NO 17
<211> LENGTH: 22
<212> TYPE: RNA
<213> ORGANISM: Homo sapiens

<400> SEQUENCE: 17
uagcuuauca gacugauguu ga                                                 22

<210> SEQ ID NO 18
<211> LENGTH: 23
<212> TYPE: DNA
<213> ORGANISM: artificial sequence
<220> FEATURE:
<223> OTHER INFORMATION: target

<400> SEQUENCE: 18
taaagtgctt atagtgcagg tag                                                23

<210> SEQ ID NO 19
<211> LENGTH: 23
<212> TYPE: DNA
<213> ORGANISM: artificial sequence
<220> FEATURE:
<223> OTHER INFORMATION: target

<400> SEQUENCE: 19
caaagtgctc atagtgcagg tag                                                23

<210> SEQ ID NO 20
<211> LENGTH: 22
<212> TYPE: DNA
<213> ORGANISM: artificial sequence
```

```
<220> FEATURE:
<223> OTHER INFORMATION: target

<400> SEQUENCE: 20
tagcttatca gactgatgtt ga                                              22

<210> SEQ ID NO 21
<211> LENGTH: 23
<212> TYPE: DNA
<213> ORGANISM: artificial sequence
<220> FEATURE:
<223> OTHER INFORMATION: target

<400> SEQUENCE: 21
caaagtgctt acagtgcagg tag                                             23

<210> SEQ ID NO 22
<211> LENGTH: 23
<212> TYPE: DNA
<213> ORGANISM: artificial sequence
<220> FEATURE:
<223> OTHER INFORMATION: target

<400> SEQUENCE: 22
taaggtgcat ctagtgcaga tag                                             23

<210> SEQ ID NO 23
<211> LENGTH: 23
<212> TYPE: DNA
<213> ORGANISM: artificial sequence
<220> FEATURE:
<223> OTHER INFORMATION: target

<400> SEQUENCE: 23
caaagtgctg ttcgtgcagg tag                                             23

<210> SEQ ID NO 24
<211> LENGTH: 23
<212> TYPE: DNA
<213> ORGANISM: artificial sequence
<220> FEATURE:
<223> OTHER INFORMATION: target

<400> SEQUENCE: 24
aaaagtgctt acagtgcagg tag                                             23

<210> SEQ ID NO 25
<211> LENGTH: 21
<212> TYPE: DNA
<213> ORGANISM: artificial sequence
<220> FEATURE:
<223> OTHER INFORMATION: target

<400> SEQUENCE: 25
taaagtgctg acagtgcaga t                                               21
```

MULTIPLEXED HOMOGENEOUS OLIGONUCLEOTIDE DETECTION

BACKGROUND

The present invention concerns a new kit for detecting or quantifying the amount of one or multiple nucleic acid targets in a biological sample, and a detection or quantification method using this kit.

MicroRNAs are a kind of single-strand nucleic acid of about 22 nucleotides. Most of microRNAs are involved in tissue-specific gene expression control by acting as post-transcriptional repressors through binding to 3'-untranslated regions of target messenger RNA. More than half of the human genes are regulated by one or more microRNAs (either same or different type) and one type of microRNA can have several hundreds of target genes. Physiological homeostasis of cells and tissues is maintained by complex regulation, and therefore microRNA dysregulation can lead to diseases such as cancer or cardiovascular diseases. Due to their importance in disease development, microRNAs have become next generation biomarkers for diagnosis and prognosis of such diseases. As peripheral blood contains many different nucleic acids, the sensitive detection of circulating microRNA in plasma or serum can provide easily accessible genetic information.

There is a strong demand for routine quantitative profiling of microRNA dysregulations by measuring total RNA extracts from blood and tissues or by direct serum or whole blood analysis. Northern blot analysis, microRNA microarrays, and stem-loop primer-based quantitative real-time PCR are the major clinical research techniques for the search and identification of microRNAs as biomarkers for diseases.

Various other technologies for direct and sensitive detection of microRNA have been developed, including electrochemistry, surface enhanced Raman spectroscopy (Abell et al., 2012), surface plasmon resonance (Šípová et al., 2010), total internal reflection ellipsometry (Le et al., 2012), quartz crystal microbalance (Chen et al., 2009), and nanoparticle, nanowire (Zhang et al., 2009), and nanopore based technologies (Jain et al., 2013). Although some of these techniques can even distinguish single base pair mismatches under idealized experimental conditions, a common drawback is lacking applicability for real-life clinical diagnostics. In such a realistic detection scenario, an ideal microRNA biosensor must be able to distinguish multiple unique sequences as well as highly similar microRNAs in a complex sample, containing many different microRNAs (and precursor microRNAs) at different concentrations. Biofouling problems of solid supports, low throughput, difficulty in upscaling, and time-consuming and labor-intensive washing steps further limit the application of these technologies as standard tools in clinical diagnostics. A commercial technology for multiplexed microRNA (and other RNAs) detection using fluorescence barcoding is "Nanostring" (Kulkarni et al., 2001). However, this heterogeneous technology requires long incubation and separation steps and dedicated equipment, which are two of the main drawbacks of this technology for easily applicable clinical diagnostics.

WO2005/103298 describes a method for the simultaneous detection of a plurality of distinct target non-coding RNAs, such as microRNA or siRNA. Said method uses, for each target nucleic acid, (i) a first probe comprising a complementary nucleic acid of said target nucleic acid and a first signal generator to generate a first detectable signal and (ii) a second probe comprising a complementary nucleic acid of said target nucleic acid and a second signal generator to generate a second detectable signal. The presence of said plurality of target non-coding RNAs is determined by measuring the first and second detectable signal.

US2011/0033855 provides a similar method for quantifying nucleic acid molecules, such as microRNA, siRNA, in a nucleic acid-containing sample by utilizing fluorescence resonance energy transfer and a photocrosslinking reaction. Said method uses a first nucleic acid molecule probe comprising a sequence complementary to the target nucleic acid molecule and conjugated with a first marker, and a second nucleic acid molecule probe comprising a sequence complementary to the first nucleic acid molecule probe and conjugated with a second marker. However, this method does not overcome the drawback of prior art.

In fact, the short lengths (approximately 22 nucleotides) and strong sequence similarities are disadvantageous for the development of specific and sensitive microRNA detection technologies. Large melting temperature difference due to the sequence variability among microRNAs have made hybridization-based capturing probes difficult to apply for large scale expression profiling (de Planell-Saguer & Rodicio, 2011). Practical issues of pre-amplification in clinical setups, the requirement of microRNA labelling or indirect amplification, and complementary DNA conversion steps (often the primary cause of variations) are among the main problems for establishing the standard technologies as robust tools for real-life clinical diagnostics (Gao et al., 2013).

Consequently, there is still a great need to develop specific and efficient assays for detecting or quantifying short nucleic acids, with labelled probes which are homogeneous (e.g., no washing and separation steps), sensitive (detection of clinically relevant concentrations), specific (e.g., discrimination of very similar sequences in a complex mixture), fast (liquid phase binding kinetics and quick measurement), reproducible (ratiometric measurement), robust (stable sensing properties of bioconjugates), storable (e.g., stable lyophilized bioconjugates within an assay kit format), versatile (generic format for many microRNAs, facile bioconjugate production/purification), and multiplexed (simultaneous measurement of several microRNAs).

SUMMARY

The present invention is to provide a kit for detecting or quantifying the amount of one or multiple nucleic acid targets of 10-40 nucleotides, in a sample obtained from biological fluid, from an in vitro cell culture or from a tissue, from plants, from yeast, from bacteria or from exosomes.

Said kit is constituted by:
(i)) one universal energy donor probe, constituted by:
  an oligonucleotide named Nd-D of 5-100, in particular 10-40, nucleotides, and
  optionally, an overhang oligonucleotide named F1 of 1-50, in particular 1-10, nucleotides,
  said oligonucleotide Nd-D, when the oligonucleotide F1 is not present in said universal energy donor probe, or said oligonucleotide F1 when it is present in said energy donor probe, being labelled by a luminescent material with an excited-state lifetime of more than 50 ns as energy donor,
(ii) at least one universal energy acceptor probe, each one being constituted by:
  an oligonucleotide named Nd-A of 5-100, in particular 10-40, nucleotides, and
  optionally, an overhang oligonucleotide named F2 of 1-50, in particular 1-10, nucleotides, said oligonucleotide Nd-A, when the oligonucleotide F2 is not present in said universal energy acceptor probe, or said oligonucleotide F2 when it is present in said universal energy acceptor probe, being labelled by a luminescent material as energy acceptor, said oligonucleotide Nd-A and said luminescent material being exclusive for each said universal energy acceptor probe, (iii) at least one couple of two adaptors, whose number is equal to that of universal energy acceptor probes, each couple of two adaptors being complementary to one unique nucleic acid target in said sample, one unique universal energy acceptor probe and the universal energy donor probe, each couple of adaptors being constituted by:

(a) a first adaptor, which is an oligonucleotide comprising:
- a fragment named PRB-D of at least 5 nucleotides whose sequence is completely complementary to that or a part of oligonucleotide Nd-D, and
- a fragment named TGT-D of at least 3 nucleotides, whose sequence is completely complementary to that of a first part of said nucleic acid target, said first part being situated at 3' or 5' end of said nucleic acid target, and (b) a second adaptor, which is an oligonucleotide comprising:
- a fragment named PRB-A of at least 5 nucleotides whose sequence is completely complementary to that or a part of oligonucleotide Nd-A, and
- a fragment named TGT-A of at least 3 nucleotides, whose sequence is completely complementary to that of a second part of said nucleic acid target, said second part being situated at another end of said nucleic acid target, each extremity of second part of said nucleic acid target being situated outside of aforementioned first part of said nucleic acid target, (iv) optionally, a ligase with eventually a polymerase, and
(v) optionally, a reaction buffer.

Contrary to all expectations, the Inventors of the present invention overcome the drawback of the prior technique by designing separately a couple of adaptors for recognizing nucleic acid targets and the energy donor/acceptor probes for reporting the presence of nucleic acid targets. The kit of the present invention provides a great technical advantage compared to prior technique: firstly, the adaptors and the energy donor/acceptor probes are physically dissociated, which makes the probes to be used as universal probes, irrespective of nucleic acid targets of the sample; secondly, the use of a couple of adaptors for each nucleic acid target, instead of one complementary probe per target, increases the specificity of sequence recognition and the distinction between very similar target sequences, such as two microRNAs.

In the presence of a nucleic acid target, the couple of adaptors of said target hybridizes respectively with said nucleic acid target and yields semi-stable adaptors-target binding at constant working temperature. The semi-stable complexes are transferred into stable double-stranded complexes by ligase or polymerase. Only these stable double-stranded adaptors-target complexes allow for efficient energy transfer between the luminescent material of energy donor probe and the luminescent material of energy acceptor probe, because the signal relating to energy transfer is only established upon stable and specific binding of both adaptor (hybridized with their respective probe) to the target.

The term "nucleic acid target" includes DNA or RNA. Said nucleic acid target may be either a single-stranded nucleic acid or a double-stranded nucleic acid. Examples of nucleic acid target of 10-40 nucleotides can include microRNAs, siRNAs, single-stranded DNAs, DNA type or RNA type synthetic oligonucleotides, cDNAs, PCR amplified products, or fragments of genomic DNA or of mRNA.

By "oligonucleotide" is meant a short single-stranded DNA or RNA. An oligonucleotide used in the present invention may be a synthetic oligonucleotide, whose sequence can be designed with the help of conventional sequence design software.

By "energy donor" is meant a material which, in its electronic excited state, may transfer energy to an energy acceptor. An energy donor may be excited by an exterior energy, such as the light, chemical reaction, biochemical reaction, electricity, magnetism, mechanics or fraction.

By "energy acceptor" is meant a material, which can physically be excited by the energy transferred from an energy donor.

The term "universal energy donor/acceptor probe" means that said energy donor/acceptor probe is suitable to be directly applied to any nucleic acid target without sequence modification or adaptation.

The type of energy transfer between the energy donor and the energy acceptor of the present invention can be any type known in the prior art, such as dexter transfer, charge transfer, electron transfer, Förster/fluorescence/bioluminescence/chemiluminescence resonance energy transfer (FRET/BRET/CRET), nanosurface energy transfer (NSET), DMPET, plasmonic coupling or singlet oxygen transfer (Hildebrandt 2014).

According to a particular embodiment of the invention, the type of energy transfer enabled by the energy donor and the energy acceptor of the present invention is Forster resonance energy transfer (FRET), named also fluorescence resonance energy transfer, for which the excitation spectrum of energy acceptor should be at least partially overlapped by the emission spectrum of energy donor.

In accordance with the present invention, the energy donor and the energy acceptor are separated in an appropriate distance for enabling energy transfer from one to another. The distance between them is extremely important for the energy transfer efficiency (which is dependent on the distance to the power of −6). For example, one skilled in the art knows that the FRET efficiency can be adjusted by designing donor-acceptor distances between ca. 1 and 15 nm.

The presence of oligonucleotide F1 in a universal energy donor and that of oligonucleotide F2 in an energy acceptor are facultative and oligonucleotides F1 and F2 are not necessarily both presenting a couple of energy donor/acceptor probes. Moreover, the lengths of F1 and F2 can be equal or different. These variations make it possible to adjust the distance between the energy donor and the energy acceptor.

In a double-stranded complex formed by an energy donor probe, an energy acceptor probe, a nucleic acid target and a couple of adaptors the oligonucleotides F1 and F2, in case they are present, are adjacent to one another. In other words, while the energy donor probe is situated at 3' end of the nucleic acid target and the energy acceptor probe is situated at 5' end of said target, the oligonucleotide F1 of energy donor probe is at 5' end of this probe and the oligonucleotide F2 of energy acceptor probe is at 3' end of this probe; while the energy donor probe is situated at 5' end of the nucleic acid target and the energy acceptor probe is situated at 3' end of said target, the oligonucleotide F1 of energy donor probe is at 3' end of this probe and the oligonucleotide F2 of energy acceptor probe is at 5' end of this probe.

Moreover, in an aforementioned double-stranded complex, the energy donor of the energy donor probe is adjacent to the energy acceptor of the energy acceptor probe. In other words, while the energy donor probe is situated at 3' end of the nucleic acid target and the energy acceptor probe is situated at 5' end of said target, the energy donor is at 5' end of energy donor probe and the energy acceptor is at the 3' end of energy acceptor probe; while the energy donor probe is situated at 5' end of the nucleic acid target and the energy acceptor probe is situated at 3' end of said target, the energy donor is at the 3' end of energy donor probe and the energy acceptor is at 5' end of energy acceptor probe.

In an aforementioned double-stranded complex, the fragment TGT-D of the first adaptor of the couple and the fragment TGT-A of the second adaptor of the same couple are also adjacent to one another.

In a couple of adaptors, the fragments TGT-D and TGT-A recognize a nucleic acid target due to their nucleic sequence complement to at least a part of said nucleic acid target; the fragments PRB-D and PRB-A recognize respectively at least a part of an energy donor probe or an energy acceptor probe due to their nucleic sequence complement.

According to the present invention, an adaptor may comprise at least a segment of nucleotides which is neither complementary with its nucleic acid target nor with an energy donor/acceptor probe.

In a couple of adaptors according to the present invention, the fragments TGT-D and PRB-D of the first adaptor, or the fragments TGT-A and PRB-A of the second adaptor, may be separated by a segment of nucleotides or be linked directly by a phosphodiester bond.

By "each extremity of second part of said nucleic acid target being situated outside of aforementioned first part of said nucleic acid target" is meant that the first and the second parts of said nucleic acid target do not contain same segment of said nucleic acid target. The first part and the second part are separated by 0 to 15 nucleotides.

In an embodiment of the invention, the universal energy donor probe of the kit of the invention is constituted by an oligonucleotide named Nd-D of 10-40 nucleotides, and optionally, an overhang oligonucleotide named F1 of 1-10 nucleotides; the universal energy acceptor probe of the kit of the invention is constituted by an oligonucleotide named Nd-A of 10-40 nucleotides, and optionally, an overhang oligonucleotide named F2 of 1-10 nucleotides.

In an embodiment of the invention, the first part is directly linked to the second part by a phosphodiester bond.

According to this embodiment, the couple of adaptors for a nucleic acid target comprises:
(a) a first adaptor, which is an oligonucleotide comprising:
  a fragment PRB-D of at least 5 nucleotides whose sequence is completely complementary to that or a part of oligonucleotide Nd-D, and
  a fragment TGT-D of at least 3 nucleotides, whose sequence is completely complementary to that of a first part of said nucleic acid target, said first part being situated at 3' or 5' end of said nucleic acid target, and
(b) a second adaptor, which is an oligonucleotide comprising:
  a fragment PRB-A of at least 5 nucleotides whose sequence is completely complementary to that or a part of oligonucleotide Nd-A, and
  a fragment TGT-A of at least 3 nucleotides, whose sequence is completely complementary to that of the remaining part of said nucleic acid target.

In this case, after hybridization of a couple of adaptors with their nucleic acid target, there is a nick between free 3' end of one adaptor of the couple and free 5' end of another adaptor of the couple. This sequence nick could be sealed by a ligase.

Said ligase can be a DNA or RNA ligase, which catalyses the ligation of a 5' phosphoryl-terminated nucleic acid to a 3' hydroxyl-terminated nucleic acid through the formation of a 3'→5' phosphodiester bond.

Said DNA ligase can be any DNA ligase known in prior art or newly developed ligase. Examples of DNA ligases that can be mentioned are, in particular, T3, T4 or T7 DNA ligase.

Said RNA ligase can be any RNA ligase known in prior art or newly developed ligase, in particular T4 RNA ligase.

In another embodiment of the invention, said first part and said second part are separated by a segment of 1 to 15 nucleotides of said nucleic acid target.

In this case, after hybridization of a couple of adaptors with their nucleic acid target, there is a gap of 1 to 15 nucleotides between free 3' end of one adaptor of the couple and free 5' end of another adaptor of the couple. The sequence gap is bridged by a conventional DNA polymerase having this function, such as DNA polymeraseβ, the nick is then sealed by a ligase.

In order to ensure enzyme activity of ligase or polymerase, one skilled in the art knows that ligation or DNA synthesis reaction should be carried out in a suitable buffer.

According to an embodiment of the present invention, when the kit comprises a ligase, said kit comprises also a ligase reaction buffer, containing at least ATP and $Mg^{2+}$ which are essential for ligase activity, and optionally any other component which can optimise ligase activity.

According to another embodiment of the present invention, when the kit comprises a polymerase, said kit comprises also a polymerase reaction buffer, containing at least ATP, GTP, TTP, CTP, $MgCl_2$, and optionally any other component which can optimise polymerase activity.

According to the present invention, the melting temperature of fragment TGT-D or TGT-A of adaptors and its complementary target sequence is significantly lower than that of PRB-D or PRB-A of adaptors and its complementary adaptor sequence, which ensures the stability of the double-stranded structure, formed by adaptors and energy donor/acceptors probes.

In a particular embodiment of the present invention, the fragment TGT-D or TGT-A of adaptor and its complementary target sequence has a melting temperature in the rage of 15° C.-65° C., in particular of 20° C.-45° C., and the fragment PRB-D or PRB-A of adaptors and its complementary adaptor sequence has a melting temperature higher than 50° C., in particular higher than 65° C.

According to an embodiment of the invention, the kit of the present invention comprises more than one energy acceptor probe.

The term "said luminescent material being exclusive for each said universal energy acceptor probe" means that energy acceptor of each energy acceptor probe of the same kit is different in its absorption and/or emission spectrum.

The distinction of emission spectra from different energy acceptors in the same kit makes it possible to carry out a sensitive multiplexed assay, based on the energy transfer from one energy donor to different energy acceptors.

The number of nucleic acid targets which may be distinguished by a kit according to the invention is determined by the number of couples of adaptors and of energy acceptor probes in said kit. In a kit of the present invention, a combination of an energy donor probe, a specific energy acceptor probe and a specific couple of adaptors, which is intended to determine or quantify a specific nucleic acid target, is named a "sensor" of said nucleic acid target.

In a particular embodiment of the present invention, the nucleic acid target of 10-40 nucleotides is chosen from a microRNA, a siRNA, a ssDNA (single-stranded DNA) or a mixture thereof.

By "biological fluid" is meant a liquid contained, excreted or secreted from a living animal or plant, for example: blood, different fraction of blood, lymph, bile, saliva, exudates. In a preferred embodiment of the present invention, the biological fluid is a human or animal origin fluid chosen from serum, inactivated serum, plasma, or blood.

By "tissue" is meant a human, animal or vegetal tissue. In a particular embodiment of the invention, the sample of a tissue is a sample obtained by biopsy or during surgical operation. In a more particular embodiment, the tissue is a tumoral tissue obtained by biopsy or during surgical operation from a patient suffering from a cancer, or suspected to develop a cancer.

In a particular embodiment of the invention, the energy donor probe of the kit contains a luminescent material with long exited-state lifetime as energy donor. The long-lived photoluminescence (PL) emitted by this type of energy donor can be used for time-gated PL detection, which efficiently supresses all background-fluorescence, thus leading to highly sensitive detection.

According to a particular embodiment of the invention, the luminescent material with excited-state lifetime as energy donor of has more than 50 ns of excited-state lifetime. Said luminescent material is chosen from a lanthanide ion such as $Tb^{3+}$, $Eu^{3+}$, $Sm^{3+}$, $Dy^{3+}$, $Er^{3+}$, $Tm^{3+}$ or $Ho^{3+}$ or a transition metal such as Ru, Ir, Os, Pt or Re, or a long-lifetime fluorophore such as fluorazaphores (Hötzer et al., 2012), or a long-lifetime nanoparticle such as semiconductor quantum dots or quantum rods or a combination thereof.

According to a particular embodiment, said luminescent material as energy donor is $Tb^{3+}$, or in particular a Lumi4®-Tb complex, which has an extremely long excited-state lifetime of about 2.7 ms. Lumi4-Tb can be efficiently excited in the UV (e.g., 337 nm emission of a nitrogen laser), which leads to mainly four bright and narrow photoluminescence (PL) emission bands in the 475 nm to 640 nm wavelength range.

By "quantum dot" is meant an inorganic semiconductor nanoparticle, including possible organic coatings, having a diameter from 1 nm to 100 nm, particularly from 5 nm to 40 nm.

By "quantum rod" is meant a rod shaped semiconductor nanocrystal, including possible organic coatings, with diameters ranging from 2 to 15 nm and with lengths ranging from 5 to 200 nm (Fu et al., 2007).

The quantum dots or quantum rods used in the present invention can be any long-lifetime quantum dot or quantum rods described in prior art, such as Cd-based or In-based quantum dots or quantum rods, in particular CdSe—ZnS core-shell nanoparticles with an additional organic coating.

According to a particular embodiment of the invention, a luminescent material used as an energy acceptor is an organic fluorophore, such as pyrene-, naphthalene-, coumarin-, fluorescein-, rhodamine- or cyanine-based dyes, or a non-fluorescent dark quencher, or a polymeric or dendrimeric dye, or a nanoparticle such as semiconductor quantum dot or quantum rod, or a naturally occurring fluorophore such as fluorescent protein or light harvesting complex, or a combination thereof.

A "non-fluorescent dark quencher" refers to a material which does not emit fluorescence in excited-state. Examples of non-fluorescent dark quencher to be cited are dabsyl (dimethylaminoazobenznesulfonic acid), BBQ650 or BHQ-2 (Holzmeister et al., 2014).

As fluorescent protein, for example GFP, EGFP, YFP, CFP, BFP, dsRed, and mCherry (and derivates of the aforementioned) can be mentioned.

By "light harvesting complex" is meant alight collecting protein such as phycobili proteins, in particular b-phycoerythrin, R-phycoerythrin, and allophycocyanin and derivates thereof.

In order to carry out time-gated PL detection of the FRET-quenched PL decay time of the donor via acceptor PL, the excited-state lifetime of energy acceptor needs to be at least ten times shorter than that of energy donor.

In preferred embodiment, the present invention concerns a kit for detecting and quantifying the amount of five single-strand nucleic acid targets of 10-40 nucleotides in a sample obtained from biological fluid, from an in vitro cell culture, from a tissue, from plants, from yeast, from bacteria or from exosomes, constituted by:

(i)) one universal energy donor probe, constituted by:
    an oligonucleotide Nd-D of 5-100, in particular 10-40, nucleotides, and
    optionally, an overhang oligonucleotide F1 of 1-50, in particular 1-10, nucleotides,
    said oligonucleotide Nd-D, when the oligonucleotide F1 is not present in said universal energy donor probe, or said oligonucleotide F1 when it is present in said universal energy donor probe, being labelled by a Tb complex as energy donor, (ii) live universal energy acceptor probes, each one being constituted by:
    an oligonucleotide Nd-A of 5-100, in particular 10-40, nucleotides, and
    optionally, an overhang oligonucleotide F2 of 1-50, in particular 1-10, nucleotides,
    said oligonucleotide Nd-A, when the oligonucleotide F2 is not present in said universal energy acceptor probe, or said oligonucleotide F2 when it is present in said universal energy acceptor probe, being labelled by an organic fluorophore as energy acceptor, said oligonucleotide Nd-A and said organic fluorophore being exclusive for each said universal energy acceptor probe, (iii) five couples of two adaptors, each couple being complementary to one unique single-strand nucleic acid target in said sample, one unique universal energy acceptor probe and the universal energy donor probe, each couple of adaptors being constituted by:
    (a) a first adaptor, which is an oligonucleotide constituted by:
        a fragment PRB-D, whose sequence is completely complementary to that of oligonucleotide Nd-D, and
        a fragment TGT-D of at least 3 nucleotides, whose sequence is completely complementary to that of a first part of said single-strand nucleic acid target, said first part being situated at 5' or 3' end of said single-strand nucleic acid target, and
    (b) a second adaptor, which is an oligonucleotide constituted by:
        a fragment PRB-A, whose sequence is completely complementary to that of oligonucleotide Nd-A, and
        a fragment TGT-A at least 3 nucleotides, whose sequence is completely complementary to that of the remaining part of said single-strand nucleic acid target, (iv) optionally, a ligase with eventually a polymerase, and
(v) optionally, a reaction buffer.

The present invention is also to provide a kit of the present invention, which is used for detecting or quantifying nucleic acid-based biomarkers, such as single nucleotide polymorphisms (SNP), which play an important role in the diagnosis and therapy of genetic diseases, in typing and tracing sources of infectious agents, in forensics.

The present invention is also to provide a method for detecting or quantifying the amount of one or multiple single-strand nucleic acid targets of 10 to 40 nucleotides, in a sample obtained from a biological fluid, from an in vitro cell culture or from a tissue, from plants, from yeast, from bacteria or from exosomes, with the help of aforementioned kit.

The short nucleic acid target detection method of the present invention does not require any washing or separation steps and has been designed for its application on a commercial clinical diagnostics fluorescence microplate reader. The integration of different hybridization and ligation/DNA synthesis reaction steps for probe-target recognition allows for a constant and low working temperature, which avoids technical adaption to different RNA or DNA melting temperatures and makes the assay insensitive to precursor microRNA interferences.

The method of the present invention comprises the steps of:

(i) adding to said sample or a solution extracted from said sample, the aforementioned kit and optionally, a ligase and eventually a polymerase, and/or a reaction buffer when the kit does not comprise said enzyme and/or said buffer, to form a complex having stable double-strands, (ii) measuring photoluminescence emission intensities issued from a universal energy donor and different universal energy acceptors, (iii) comparing photoluminescence emission intensities obtained in previous step with pre-established standard intensities to determine the amount of targeted oligonucleotide nucleic acid target.

The method of the invention may be applied in case of FISH (Fluorescence in situ hybridization), wherein the sample used in step (i) may be a sample of tissues or cells prepared and fixed according to a conventional protocol.

The sample used in step (i) may also be a DNA/RNA extraction obtained according to a conventional protocol.

The photoluminescence emission intensity measurements can be carried out by any conventional instrument, such as fluorescence spectrometers or fluorescence microscopes. In the case of time-resolved or time-gated PL measurements time-resolved detectors such as photomultiplier tubes (PMTs) or intensified CCD (ICCD) cameras are necessary.

Pre-established standard intensities (so-called assay calibration curves) are determined from a series of samples containing all the sensors of the kit according to the invention and different defined concentrations of the different nucleic acid targets.

In a particular embodiment, the method of the present invention comprises further a step (ii'), which is between step (ii) and step (iii), of measuring biological and spectral crosstalk to calculate normalized photoluminescence emission intensities.

By "spectral crosstalk" is meant the detection of energy donor PL in energy acceptor detection channels as well as the detection of one energy acceptor in another energy acceptor detection channel or the donor detection channel.

By "biological crosstalk" is meant the detection of one nucleic acid target by a couple of adaptors designed for another nucleic acid target, due to hybridization of the other nucleic acid target to that couple of adaptors. E.g. a biological crosstalk may happen in case of detection of two very similar microRNAs, such as miRNA-20a and miRNA-20b.

The spectral crosstalk correction may be carried out according to the method described in Geißler et al. (2013). This method uses a matrix, which includes all possible crosstalks from the different fluorophores in the different detection channels. This matrix is multiplied with the PL intensities measured in each detection channel to efficiently correct for the significant spectral crosstalk.

The correction of biological and spectral crosstalk uses a similar method through the generation of biological and spectral matrices by testing in a sample the photoluminescence emission intensity produced by all sensors with all nucleic acid targets to be determined. For each target, the fraction of bio-spectral crosstalk of energy donor and energy acceptors to the non-corresponding detection channels is measured.

According to a particular embodiment of the method of the present invention, photoluminescence emission intensity of a universal energy donor and each universal energy acceptor are measured in a specific time window after light excitation.

The determination of beginning time and the length of this time window are known to one skilled in the art, and are dependent on the PL decay time of the energy donor and acceptor, which is also strongly dependent on the donor-acceptor distance as mentioned above and on the detection system. The most important aspect for selecting the time window is the acquisition of a strong specific (energy transfer) PL intensity and a weak non-specific (background) PL intensity, or in other words a high signal to noise ratio. For example for a Lumi4-Tb donor measured on a time-resolved fluorescence plate reader the delay after the excitation pulse is usually selected between 5 and 500 microseconds and the gate (width of time window) between 20 and 5000 microseconds.

In order to ensure the hybridization and the stability of the double-stranded complex formed by nucleic acid target, the couple of adaptors, the energy donor probe and the energy acceptor probe, the step (i) of the method of the present invention is carried out in a temperature lower than that of melting temperature of PRB-D and PRB-A.

In a particular embodiment, the step (i) of the method of the present invention is carried out at a temperature comprised from 10° C. to 80° C.

In a preferred embodiment, the step (i) is carried out at room temperature, for example lower than 37° C., which avoids the interference of precursor microRNAs.

In a particular embodiment, the present invention concerns a method for detecting or quantifying the amount of one or multiple microRNAs in a sample.

In another particular embodiment, when the nucleic acid target to be determined or quantified in a sample is a siRNA, or a short double-stranded DNA, said method of the invention comprises before the step (i) a step for denaturing double-stranded nucleic acid and preparing single strand nucleic acid target.

In a particular embodiment, the method of the present invention is used for diagnosis or prognosis of a disease, such as a cancer or cardiovascular diseases.

In another embodiment, the method of the present invention is also used for in vitro diagnosis or prognosis of a disease, such as a cancer or cardiovascular diseases.

The present invention is illustrated in detail in following figures and examples.

BRIEF DESCRIPTION OF THE DRAWINGS

FIG. 1a illustrates the principal components of a sensor of the invention, which is composed of two probe oligonucleotides (probe oligos) and two adaptor oligonucleotides (adaptor oligos). The probe oligos consist in a Tb-donor or a dye-acceptor, adaptable poly-nucleotide overhangs (F1 and F2), and a specific hybridization sequence. The adaptor oligos consist of a specific sequence for the donor (PRB-D) or acceptor (PRB-A) probe oligos, and a sequence (TGT-A or TGT-B), which is specific to a part of the target. A ligase is used for the ligation of TGT-D and TGT-A (using ATP in the solution and a 5'-phosphate (P) modification integrated in TGT-A). Multiplexing of three different targets in a single sample requires three different dye probe oligos and the adaption of the adaptor oligos to the probe oligos and the targets.

FIG. 1b: Mixing of a sensor and a target leads to the formation of stable probe-adaptor double-strands (melting temperatures $T_m$>50° C.) and the formation of semi-stable adaptor-target complexes ($T_m$ target- and assay-specific), with an adaptor nick over the target splint. Ligation of this nick leads to the formation of stable double-strands.

FIG. 1c: Stable sensor-target complexes ($T_m$>50° C.) allow Tb-to-dye FRET for multiplexed time-gated photoluminescence detection of nucleic acid biomarkers. FIG. 1d: FRET kit containing three sensors respectively named Tb-miRNA-20a-Cy3.5 (left), Tb-miRNA-20b-Cy5 (middle) and Tb-miRNA-21-Cy5.5 (right) for triplexed micro-RNA detection (miRNA-20a, miRNA-20b, miRNA-21). Labels on the different parts of the single sensors (P=probe, A=adaptor) describe the persistent or changing parts from one sensor to the other (A4a, A4b, A4c and A3b are RNA, all other parts are DNA).

FIG. 1e: Magnification of the different bases in A4a-miRNA-20a and A4b miRNA-20b base pairing.

FIG. 2a: Absorbance spectra (left ordinate) of the probe-oligos containing Tb-donor and the acceptor dyes Cy3.5, Cy5 and Cy5.5. Area-normalized PL spectrum of Tb (grey in the background) is shown for visualization of donor-acceptor spectral overlap. Förster distances were 6.5 nm, 6.3 nm and 5.7 nm for Tb-Cy3.5, Tb-Cy5 and Tb-Cy5.5, respectively.

FIG. 2b: PL emission spectra (normalized to unity at their respective peaks) of Tb (black), Cy3.5, Cy5 and Cy5.5. Transmission spectra of Tb-donor and dye-acceptor detection channels are show in grey in the background.

FIGS. 2c and 2d are representative PL decay curves measured in the Tb-detection channel (FIG. 2c) and in the Cy3.5 detection channel (FIG. 2d) for the sensor Tb-miRNA-20a-Cy3.5. FRET OFF curves were detected at the absence of target (cf. FIG. 1a) and represent pure Tb PL. The FRET ON curves were detected in the presence of target and represent Tb PL quenching (FIG. 2c) and Cy3.5 PL sensitization (FIG. 2d) due to Tb-to-Cy3.5 FRET. The grey areas represent the time-windows for which time-gated PL detection was performed simultaneously in both channels during the assays. Because freely diffusing Tb-probe-adaptor and dye-probe-adaptor oligos are always present in the assays (homogeneous assay—no washing), the addition of low target concentrations leads to relatively weak FRET-quenching of Tb PL (high background from free Tb-donors). On the other hand the acceptor-dyes are strongly FRET-sensitized (zero background from free dye-acceptors and low background from free Tb-donors).

FIGS. 3a and 3b show selectivity of the kit of invention for very similar sequences. High selectivity of two sensors: Tb-miRNA-20a-Cy3.5 (FIG. 3a) and Tb-miRNA-20b-Cy5 (FIG. 3b), of a kit according to the invention, for their respective targets is demonstrated by high FRET-ratios for matched targets and very low FRET-ratios for mismatched targets, which are equal to the background FRET-ratios (controls; Tb: only Tb-donor probe oligo; Tb+Cy3.5/5: both probe oligos; no target: complete kit without target) for double-stranded T4 RNA ligase concentrations up to 0.1 CEU. Optimal selectivity conditions are provided by 0.1 CEU ligase. Higher ligase concentrations (1 CEU) lead to increased mismatch detection.

FIGS. 4a, 4b and 4c show respectively the calibration curves of the targets miRNA-20a, miRNA-20b and miRNA-21 before (left) and after (right) bio-spectral crosstalk correction. The abscissa corresponds to the concentration of nucleic acid target in the sample. Squares correspond to the signals obtained by sensor Tb-miRNA-20b-Cy5. Circles correspond to the signals obtained by sensor Tb-miRNA-20a-Cy3.5. Triangles correspond to the signals obtained by sensor Tb-miRNA-21-Cy5.5. The calibration curves show the target-specific signal intensities over increasing target concentrations. All assays contain all three sensors but only one target (with increasing concentration). Assays with all targets present in the samples at different concentrations led to similar calibration curves, which are shown in FIGS. 7a, 7b and 7c for micro-RNA and FIGS. 8a, 8b, and 8c for ssDNA. Comparing the left with the right graphs shows the necessity of an efficient correction algorithm in order to allow a precise multiplexed measurement of three microRNAs at sub-nanomolar concentrations.

FIG. 5a represents 9 samples (S1 to S9) containing varying concentrations between 50 and 500 pM (dotted lines indicate the known concentrations) were measured with the bio-spectral crosstalk corrected homogeneous multiplexed assays. In order to demonstrate the high precision of the sensors in a kit of the invention for a single measurement (2.5 s per measurement), each sample was prepared and measured only once. The error bars present the errors from bio-spectral crosstalk correction. Deviations from the dotted lines are due to experimental errors (pipetting and/or excitation intensity). FIGS. 5b, 5c and 5d correspond to the calibration curves after bio-spectral crosstalk correction for the targets miRNA-20a (FIG. 5b), miRNA-20b (FIG. 5c) and miRNA-21 (FIG. 5d) in 7.5 μL serum samples. The abscissa corresponds to the concentration of nucleic acid target in the sample. The calibration curves show the target-specific signal intensities over increasing target concentrations. All assays contain all three sensors of a kit of the invention but only one target (with increasing concentration). For better comparison to the buffer-based assays the abscissa displays the concentrations within the 150 μL sample volumes (concentrations must be multiplied by 20 for the target concentrations within the 7.5 μL serum samples). Results for ssDNA can be found in FIGS. 9a to 9d.

FIG. 6a and FIG. 6b illustrate high selectivity of sensor Tb-ssDNA-20a-Cy3.5 (FIG. 6a) and sensor Tb-ss-DNA-20b-Cy5 (FIG. 6b) for their respective targets by high FRET-ratios for matched targets (ssDNA-20a in FIG. 6a and ssDNA-20b in FIG. 6b) and very low FRET-ratios for mismatched targets (ssDNA-20b in FIG. 6a and ssDNA-20a in FIG. 6b), which are equal to the background FRET-ratios (controls; Tb: only Tb-donor probe oligo; Tb+Cy3.5/5: both probe oligos; no target: complete kit without target) for double-stranded DNA ligase concentrations up to 2 CEU. Optimal selectivity conditions are provided by 2 CEU ligase. Higher ligase concentrations (20 CEU) lead to increased mismatch detection. FIG. 6c and FIG. 6d illustrate selectivity of sensorsTb-ssDNA-20a-Cy3.5 (FIG. 6c) and Tb-ssDNA-20b-Cy5 (FIG. 6d) for their respective targets against other ssDNA targets (all displayed on the abscissa) with very similar sequences (cf. Table 1) to ssDNA-20a and ssDNA-20b.

FIG. 9a shows 9 samples (S1 to S9) containing varying concentrations between 50 and 500 pM (dotted lines indicate the known concentrations) were measured with the bio-spectral crosstalk corrected homogeneous mutiplexed assays. FIGS. 9b, 9c and 9d illustrate calibration curves after bio-spectral crosstalk correction for the targets ssDNA-20a (FIG. 9b), ssDNA-20b (FIG. 9c) and ssDNA-21 (FIG. 9d) in 7.5 µL serum samples. The abscissa corresponds to the concentration of nucleic acid target in the sample. Squares correspond to the signals obtained by sensor Tb-ssDNA-20b-Cy5. Circles correspond to the signals obtained by sensor Tb-ddDNA-20a-Cy3.5. Triangles correspond to the signals obtained by sensor Tb-ssDNA-21-Cy5.5. The calibration curves show the target-specific signal intensities over increasing target concentrations. All assays contain all three sensors of a kit of the invention but only one target (with increasing concentration). For better comparison to the buffer-based assays the abscissa contains the concentrations within the 150 µL sample volumes (concentrations must be multiplied by 20 for the target concentrations within the 7.5 µL serum samples).

DETAILED DESCRIPTION

Example

Figure 2A:
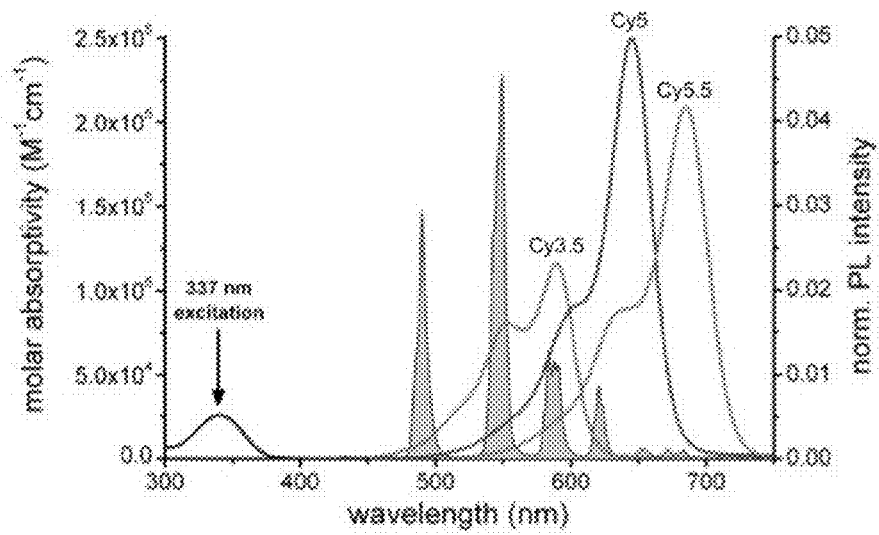
FIGS. 2a to 2d illustrate photophysical properties of a kit of the invention containing 3 sensors for carrying out FRET.

1. Materials and Methods
1.1 Materials:

Maleimide activated Lumi4® complexes (L4-mal) were provided by Lumiphore Inc. (Berkeley, Calif., USA). All chemicals were used as received. Water was purified by Purelab Option-Q equipped with bio-filter (ELGA Labwater Veolia water ST1, Antony, France) to produce nuclease free water. Non-modified oligonucleotides were purified with cartridge gold desalting method. All modified or hybrid backbone oligonucleotides were purchased HPLC purified from Eurogentec.

The adaptors were purchased from Eurogentec with specific requirement to obtain full DNA backbone or hybrid backbone (partial DNA and partial RNA backbone) as well as 5' phosphate modification. Hybrid backbone was introduced in adaptor design to make the microRNA hybridizing region conform to requirements of the ligases used in the assays (T4 DNA ligase or T4 RNA ligase2; T4 DNA ligase is efficiently ligating nicks in a dsDNA, and T4 RNA ligase2 is efficiently ligating nicks in dsRNA, it can also efficiently join nicks having 3' hydroxyl group on the nick position of DNA instead of RNA over RNA splint. This ability has been used for some of the sensors designed for microRNA in this study).

The three dye-labelled (cy3.5, cy5, cy5.5) probe oligos working as energy acceptor probe were directly purchased from Eurogentec.

The Tb-labelled probe oligos were prepared according to the protocol described in following part 1.2.

All sequences and modifications of nucleic acids used in this study are summarized in table 1.

TABLE 1

| Oligonucleotide properties (for nomenclature cf. FIG. 1d) | | | |
| --- | --- | --- | --- |
| | Sequence | modification | $T_m$ (°C.) |
| Probes | | | |
| P1 (SEQ ID NO: 1) | CGATCAGTCAGGCAAAGCGG | 5' C6 thiol | DNA/DNA: 62 |
| F1-P1 (ssDNA) (SEQ ID NO: 2) | AAAAAA-CGATCAGTCAGGCAA | 5' C6 thiol | DNA/DNA: 51 |
| P2a-F2 (SEQ ID NO: 3) | TTACTGTGCACAGAGGA-AAAAAA | 3' C7 amine | DNA/DNA: 54 |

TABLE 1-continued

Oligonucleotide properties (for nomenclature cf. FIG. 1d)

| | Sequence | modification | $T_m$ (°C.) |
|---|---|---|---|
| P2b-F2 (SEQ ID NO: 4) | TTGTGTTCCGATAGGCT-AAAAAA | 3' C7 amine | DNA/DNA: 54 |
| P2c-F2 (SEQ ID NO: 5) | AATCAAGGTAACGGACT-AAAAAA | 3' C7 amine | DNA/DNA: 52 |
| Adaptors | | | |
| A1-A3a (SEQ ID NO: 6) | CCGCTTTGCCTGACTGATCG-CTACCTGCACTAT | 3'-hydroxyl | DNA/DNA: 40<br>DNA/RNA: 38 (at 2 mM $Mg^{2+}$)<br>DNA/RNA: 41 (at 10 mM $Mg^{2+}$) |
| A1-A3b (SEQ ID NO: 7) | CCGCTTTGCCTGACTGATCG-UCAACAUCAGUC | 3'-hydroxyl | DNA/DNA: 36<br>RNA/RNA: 46 (at 2 mM $Mg^{2+}$)<br>RNA/RNA: 50 (at 10 mM $Mg^{2+}$) |
| A1-A3b (ssDNA and miRNA in serum) (SEQ ID NO: 8) | CCGCTTTGCCTGACTGATCG-TCAACATCAGTC | 3'-hydroxyl | DNA/DNA: 36<br>DNA/RNA: 26 (at 2 mM $Mg^{2+}$)<br>DNA/RNA: 29 (at 10 mM $Mg^{2+}$) |
| A4a-A2a-rest (SEQ ID NO: 9) | AAGCACUUUA-TCCTCTGTGCACAGTAA-CCCCTAACCCTCT | 5' phosphate | RNA/RNA: 30 (at 2 mM $Mg^{2+}$)<br>RNA/RNA: 34 (at 10 mM $Mg^{2+}$) |
| A4b-A2b-rest (SEQ ID NO: 10) | GAGCACUUUG-AGCCTATCGGAACACAA-CCCCTAACCCTCT | 5' phosphate | RNA/RNA: 20 (at 2 mM $Mg^{2+}$)<br>RNA/RNA: 23 (at 10 mM $Mg^{2+}$) |
| A4c-A2c-rest (SEQ ID NO: 11) | UGAUAAGCUA-AGTCCGTTACCTTGATT-CCCCTAACCCTCT | 5' phosphate | RNA/RNA: 32 (at 2 mM $Mg^{2+}$)<br>RNA/RNA: 37 (at 10 mM $Mg^{2+}$) |
| A4a-A2a-rest (ssDNA) (SEQ ID NO: 12) | AAGCACTTTA-TCCTCTGTGCACAGTAA-CCCCTAACCCTCT | 5' phosphate | DNA/DNA: 25 |
| A4b-A2b-rest (ssDNA) (SEQ ID NO: 13) | GAGCACTTTG-AGCCTATCGGAACACAA-CCCCTAACCCTCT | 5' phosphate | DNA/DNA: 30 |
| A4c-A2c-rest (ssDNA) (SEQ ID NO: 14) | TGATAAGCTA-AGTCCGTTACCTTGATT-CCCCTAACCCTCT | 5' phosphate | DNA/DNA: 21 |
| Targets | | | |
| miRNA-20a (SEQ ID NO: 15) | UAAAGUGCUUAUAGUGCAGGUAG | / | RNA/DNA: 53 (at 2 mM $Mg^{2+}$) |
| miRNA-20b (SEQ ID NO: 16) | CAAAGUGCUCAUAGUGCAGGUAG | / | RNA/DNA: 57 (at 2 mM $Mg^{2+}$) |
| miRNA-21 (SEQ ID NO: 17) | UAGCUUAUCAGACUGAUGUUGA | / | RNA/DNA: 49 (at 2 mM $Mg^{2+}$) |
| ssDNA-20a (SEQ ID NO: 18) | TAAAGTGCTTATAGTGCAGGTAG | / | DNA/DNA: 58 |
| ssDNA-20b (SEQ ID NO: 19) | CAAAGTGCTCATAGTGCAGGTAG | / | DNA/DNA: 61 |
| ssDNA-21 (SEQ ID NO: 20) | TAGCTTATCAGACTGATGTTGA | / | DNA/DNA: 57 |
| ssDNA-17 (SEQ ID NO: 21) | CAAAGTGCTTACAGTGCAGGTAG | / | DNA/DNA: 61 |
| ssDNA-18a (SEQ ID NO: 22) | TAAGGTGCATCTAGTGCAGATAG | / | DNA/DNA: 59 |
| ssDNA-93 (SEQ ID NO: 23) | CAAAGTGCTGTTCGTGCAGGTAG | / | DNA/DNA: 63 |
| ssDNA-106a (SEQ ID NO: 24) | AAAAGTGCTTACAGTGCAGGTAG | / | DNA/DNA: 61 |
| ssDNA-106b (SEQ ID NO: 25) | TAAAGTGCTGACAGTGCAGAT | / | DNA/DNA: 59 |

All sequences are written in 5'→3' direction. In case the oligonucleotides were used for ssDNA detection only, this is indicated in the oligo name (first column). "Rest" sequences are not used in the assays within this study but add flexibility in case longer acceptor probe oligos are required. Melting temperatures ($T_m$) were calculated by using Oligo Analyzer version 3.1 (Integrated DNA Technologies). $T_m$ values for DNA/DNA duplexes were calculated using parameters set to oligonucleotide concentration at 0.003 µM, $Na^+$ ion at 150 mM, $Mg^{2+}$ ion at 10 mM, dNTPs at 0 mM. $T_m$ values of RNA/DNA or RNA/RNA duplexes were calculated using parameters set to oligonucleotide concentration at 0.003 µM, $Na^+$ ion at 50 mM, $Mg^{2+}$ at 2 mM or 10 mM, dNTP at 0 mM. Calculated $T_m$ values have ±1.4° C. accuracy for DNA/DNA duplexes and ±2.7° C. accuracy for DNA/RNA or RNA/DNA or RNA/RNA duplexes. The dye modifications were not taken into consideration for Tin calculation.

HEPES (#H3375), terbium chloride (#204560), bovine serum albumin (BSA, A8806), and single stranded salmon sperm DNA (#7656) were purchased from Sigma-Aldrich (St. Louis, Mo., USA). NaCl (#S0520) and $MgCl_2$ (#M0533) were purchased from Duchefa (The Netherlands). Newborn calf serum was provided by Cezanne/Thermo Fisher Scientific (Nimes, France). Ambion®RNAsecure™ RNase inactivation reagent (RNA secure reagent, #AM7006) was purchased from Life Technologies. T4 DNA ligase (#EL0016) was purchased from Fermentas, and T4 RNA ligase2 (#M0239L) was purchased from New England Biolabs (Beverly, Mass., USA).

1.2 Tb-Donor Probes Preparation

Tb-donor probes working as energy donor probe were labelled in laboratory by the Inventors. L4-mal was reacted overnight at room temperature with purified reduced 5' thiol modified (C6 linker) probe oligos. The protocol was as follows: 50 μL of 100 μM thiol labelled probe oligo is diluted to 115 μL with D.I. water. Then 5 μL of freshly prepared 1M tris(2-carboxyethyl) phosphine (TCEP, non sulfur based reducing agent) was spiked into the solution and mixed by brief vortexing. The mixture was incubated at 50° C. for 1 hr to allow sufficient time for the protection of thiol group on the modified oligo. Then the mixture was desalted and buffer exchanged into conjugation buffer (100 mM HEPES, 1 M NaCl, pH7.4) with 0.5 mL Zeba spin columns (Pierce). The flow through containing freshly reduced thiol modified oligonucleotides was immediately mixed with 20 times molar excess amount of L4-mal (dissolved in dimethyformamide) and incubated overnight at ambient temperature. The reaction was quenched by further incubation for 10 min after addition of 1 μL β-mercaptoethanol. The conjugated L4 labelled probe oligos were then separated from excess of free L4 and other impurities by desalting of the quenched reaction mixture with a PD-10 desalting column (GE healthcare), which was pre-equilibrated with storage buffer (25 mM HEPES, 150 mM NaCl, pH7.4). All elution fractions were analyzed for concentration of oligonucleotides by monitoring the absorbance at 260 nm. The early fractions containing high concentrations of oligonucleotides were pooled to determine the final oligo concentration. Then a 1.2 molar equivalent of terbium chloride was introduced to the L4-labeled probes and incubated for at least 4 hrs at 4° C. to charge $Tb^{3+}$ ion to the L4 labeled oligo probes.

1.3 Photophysical Properties

Absorption spectra of Tb and dyes were measured on a Spectrostar Nano absorption reader (BMG Labtech). Emission spectra were measured on a FluoTime 300 fluorescence spectrometer (PicoQuant). PL decays were measured on a KRYPTOR diagnostic time-resolved fluorescence plate reader (Cezanne/Thermo Fisher Scientific).

1.4 Selectivity for Different RNA or DNA Sequences

For evaluation of the selectivity of the method and a kit of the present invention, the sensors designed respectively for nucleic acid targets: hsa-miR-20a-5p (miRNA-20a, 23 nucleotides), hsa-miR-20b-5p (miRNA-20b, 23 nucleotides) as well as the ssDNA analogues of miRNA (ssDNA-20b) and miRNA (ssDNA-20a) were tested separately with their matched target and a mismatched target. The sensor for miRNA-20a, named sensor Tb-miRNA-20a-Cy3.5, contains Tb-donor, Cy3.5 acceptor, and a couple of adaptors of sequences SEQ ID NO: 6 and 9. The sensor for miRNA-20b, named sensor Tb-miRNA-20b-Cy5, contains TB-donor, Cy5 acceptor, and a couple of adaptors of sequences SEQ ID NO: 8 and 10. The sensor for ssDNA-20a, named sensor Tb-ssDNA-20a-Cy3.5, contains Tb-donor, Cy3.5 acceptor, and a couple of adaptors of sequences SEQ ID NO: 6 and 12, The sensor for ssDNA-20b, named sensor Tb-ssDNA-20b-Cy5, contains TB-donor, Cy5 acceptor, and a couple of adaptors of sequences SEQ ID NO: 8 and 13, For all samples (150 μL) the FRET-ratios (for the detection channel corresponding to the sensor) were measured on a KRYPTOR clinical fluorescence plate reader using 100 nitrogen laser excitation pulses (5 s) per sample after an incubation of the samples at 37° C. for 2 hrs. For statistical analysis each sample was prepared once and measured three times. The sample properties were as follows (for nomenclature cf. FIG. 1 and Table 2), 1) microRNA assays: a) controls: Tb alone: 3 nM P1 in miRNA buffer (25 mM HEPES buffer, 50 mM NaCl, 2 mM $MgCl_2$, 0.4 mM ATP pH7.4+0.1% BSA; RNA secure reagent treated); Tb+Cy3.5: 3 nM P1, 6 nM P2a-F2 in miRNA buffer; Tb+Cy5: 3 nM P1, 6 nM P2b-F2 in miRNA buffer; no target in Tb-miRNA-20a-Cy3.5 sensor: 3 nM P1, 6 nM P2a-F2, 3 nM A1-A3a, 3 nM A4a-A2a in miRNA buffer; no target Tb-miRNA-20b-Cy5' sensor: 3 nM P1, 6 nM P2b-F2, 3 nM A1-A3a, 3 nM A4b-A2b in miRNA buffer; b) matched targets: miRNA-20a with Tb-miRNA-20a-Cy3.5 sensor: 3 nM miRNA-20a, 3 nM P1, 6 nM P2a-F2, 3 nM A1-A3a, 3 nM A4a-A2a in miRNA buffer; miRNA-20b with Tb-miRNA-20b-Cy5 sensor:3 nM miRNA-20b, 3 nM P1, 6 nM P2b-F2, 3 nM A1-A3a, 3 nM A4b-A2b in Mg-2 miRNA buffer; c) mismatched targets: miRNA-20b with Tb-miRNA-20a-Cy3.5 sensor: 3 nM miRNA-20b, 3 nM P1, 6 nM P2a-F2, 3 nM A1-A3a, 3 nM A4a-A2a in miRNA buffer; miRNA-20a with Tb-miRNA-20b-Cy5" sensor:3 nM miRNA-20a, 3 nM P1, 6 nM P2b-F2, 3 nM A1-A3a, 3 nM A4b-A2b in miRNA buffer; 2) ssDNA assays: a) controls: Tb alone: 3 nM F1-P1 (ssDNA) in ssDNA buffer (25 mM HEPES buffer, 150 mM NaCl, 10 mM $MgCl_2$, 1 mM ATP pH7.4+0.1% BSA); Tb+Cy3.5: 3 nM F1-P1 (ssDNA), 6 nM P2a-F2 in ssDNA buffer; Tb+Cy5: 3 nM F1-P1 (ssDNA), 6 nM P2b-F2 in ssDNA buffer; no target in Tb-ssDNA-20a-Cy3.5 sensor: 3 nM F1-P1 (ssDNA), 6 nM P2a-F2, 3 nM A1-A3a, 3 nM A4a-A2a (ssDNA) in ssDNA buffer; no target Tb-ssDNA-20b-Cy5 sensor: 3 nM F1-P1 (ssDNA), 6 nM P2b-F2, 3 nM A1-A3a (ssDNA), 3 nM A4b-A2b (ssDNA) in ssDNA buffer; b) matched targets: ssDNA-20a with Tb-ssDNA-20a-Cy3.5 sensor: 3 nM ssdNA-20a, 3 nM F1-P1 (ssDNA), 6 nM P2a-F2, 3 nM A1-A3a, 3 nM A4a-A2a (ssDNA) in ssDNA buffer; ssDNA-200 with Tb-ssDNA-20b-Cy5 sensor: 3 nM ssDNA-20b, 3 nM F1-P1 (ssDNA), 6 nM P2b-F2, 3 nM A1-A3a, 3 nM A4b-A2b (ssDNA) in ssDNA buffer; c) mismatched targets: ssDNA-20b with Tb-ssDNA-20a-Cy3.5 sensor: 3 nM ssDNA-20b, 3 nM F1-P1 (ssDNA), 6 nM P2a-F2, 3 nM A1-A3a, 3 nM A4a-A2a (ssDNA) in ssDNA buffer; ssDNA-20a with Tb-ssDNA-200-Cy5 sensor: 3 nM ssDNA-20a, 3 nM F1-P1 (ssDNA), 6 nM P2b-F2, 3 nM A1-A3a, 3 nM A4b-A2b (ssDNA) in ssDNA buffer.

1.5 Multiplexing and Bio-Spectral Crosstalk Correction

The multiplexed assays contain all three sensors of a kit according to the invention and can therefore not use the FRET-ratio as detection signal. Instead the time-gated PL intensities in the different acceptors channels are measured, then the spectral crosstalk of the Tb PL (cf. Table 2) is subtracted and finally the spectral crosstalk of the PL from the other acceptors is corrected via a matrix-assisted crosstalk correction. This method is detailed in Geißler et al. (2013). The original method was based on immunoassays, for which the biological cross-reactivity was negligible. In the study cross-reactivity needs to be taken into account and therefore the method is slightly different as outlined below. Moreover, multiplexed assays were performed under two different experimental conditions (in buffer and in serum) and for two different targets (microRNA and ssDNA), which means that four bio-spectral crosstalk correction matrices need to be generated. Time-gated intensities in the different dye channels were measured on the KRYPTOR plate reader (150 μL sample volumes) using the following sample concentrations. 1) Multiplexed microRNA assays in buffer: This assay is to evaluate a kit of the invention containing multiplexed sensors for detecting multiple microRNA targets in a sample of buffer solution. 750 pM of miRNA-20a or miRNA-20b or miRNA21 mixed with their sensors (9 nM P1, 3 nM P2a-F2, 3 nM P2b-F2, 3 nM P2c-F2, 6 nM A1-A3a, 3 nM A4a-A2a, 3 nM A4b-A2b, 3 nM A1-A3b, 3 nM A4c-A2c) in miRNA multiplexing buffer (25 mM HEPES buffer, 50 mMNaCl, 2 mM $MgCl_2$, 0.4 mM ATP, 100 µg/ml single stranded salmon sperm DNA, pH7.4+0.1% BSA; RNA secure reagent treated); 2) Multiplexed microRNA assays in serum: This assay is to evaluate a kit of the invention containing multiplexed sensors for detecting multiple microRNA targets in a serum sample. 750 pM of miRNA-20a or miRNA-20b or miRNA21 mixed with their sensors (9 nM P1, 3 nM P2a-F2, 3 nM P2b-F2, 3 nM P2c-F2, 6 nM A1-A3a, 3 nM A4a-A2a, 3 nM A4b-A2b, 3 nM A1-A3b (ssDNA and miRNA in serum), 3 nM A4c-A2c) in miRNA multiplexing buffer containing 5% of new born calf serum; 3) Multiplexed ssDNA assays in buffer: This assay is to evaluate a kit of the invention containing multiplexed sensors for detecting multiple ssDNA targets in a sample of buffer solution. 750 pM of ssDNA-20a or ssDNA-20b or ssDNA21 mixed with their sensors (9 nM F1-P1 (ssDNA), P2a-F2, 3 nM P2b-F2, 3 nM is P2c-F2, 6 nM A1-A3a, 3 nM A4a-A2a (ssDNA), 3 nM A4b-A2b (ssDNA), 3 nM A1-A3b (ssDNA and miRNA in serum), 3 nM A4c-A2c (ssDNA)) in ssDNA multiplexing buffer (25 mM HEPES buffer, 150 mMNaCl, 10 mM $MgCl_2$, 1 mM ATP, 100 µg/ml single stranded salmon sperm DNA, pH7.4+0.1% BSA). 4) Multiplexed ssDNA assays in serum: This assay is to evaluate a kit of the invention containing multiplexed sensors for detecting multiple ssDNA targets in a serum sample. 750 pM of ssDNA-20a or ssDNA-20b or ssDNA21 mixed with their sensors (9 nM F1-P1 (ssDNA), 3 nM P2a-F2, 3 nM P2b-F2, 3 nM P2c-F2, 604 A1-A3a, 3 nM A4a-A2a (ssDNA), 3 nM A4b-A2b (ssDNA), 3 nM A2-A3b (ssDNA and miRNA in serum), 3 nM A4c-A2c (ssDNA)) in heat-inactivated ssDNA multiplexing buffer containing 5% of new born calf serum.

For statistical analysis each sample was prepared three times and measured once (100 laser pulses per target, which corresponds to 5 s per target or 15 s per sample) except for miRNA assays in buffer, for which each sample was prepared once and measured three times (50 laser pulses per target, which corresponds to 2.5 s per target or 7.5 s per sample). Using the different time-gated intensities mentioned above, the four bio-spectral crosstalk correction matrices were generated (Tables 3 and 4) by normalizing the intensities of corresponding target and detection channel to unity (diagonal of the matrix) and calculating the intensities in the other detection channels relative to the intensity in the corresponding channel. In that way the relative intensities generated by each target in each detection channel are recorded in the matrix. The four matrices were numerically inverted using QtOctave 3.6.2 (GNU general public license). For all multiplexed assay experiments the corresponding bio-spectral crosstalk correction matrices (Tables 3 and 4) and the Tb spectral crosstalk factors (Table 2) were used for correcting the time-gated intensities measured in the different acceptor channels as detailed in Geißler et al.; 2013.

TABLE 2

| Spectral crosstalk fraction of Tb PL to dye channels | |
|---|---|
| Detection channel | PL fraction |
| Tb | 1 |
| Cy3.5 | 0.010 ± 0.0003 |
| Cy5 | 0.05 ± 0.0008 |
| Cy5.5 | 0.003 ± 0.00005 |

\* The time-gated PL in the Tb-channel was normalized to unity. The spectral crosstalk fractions in the dye-channels are the relative time-gated intensities compared to the Tb-channel.

TABLE 3

| Bio-spectral crosstalk of multiplexed sensor-microRNA for different experiments | | | | |
|---|---|---|---|---|
| Experiment | Detection channel | miRNA-20a (Cy3.5 dye) | miRNA-20b (Cy5 dye) | miRNA-21 (Cy5.5 dye) |
| Multiplexed microRNA assays in buffer | Cy3.5 | 1 | −0.003 ± 0.001 | −0.007 ± 0.004 |
| | Cy5 | 1.315 ± 0.021 | 1 | −0.006 ± 0.009 |
| | Cy5.5 | 0.530 ± 0.031 | 0.475 ± 0.014 | 1 |
| Multiplexed microRNA assays in serum | Cy3.5 | 1 | 0.003 ± 0.002 | 0.012 ± 0.003 |
| | Cy5 | 1.424 ± 0.019 | 1 | 0.023 ± 0.003 |
| | Cy5.5 | 0.518 ± 0.010 | 0.431 ± 0.020 | 1 |

TABLE 4

| Bio-spectral crosstalk of multiplexed sensor-ssDNA for the different experiments | | | | |
|---|---|---|---|---|
| Experiment | Detection channel | ssDNA-20a (Cy3.5 dye) | ssDNA-20b (Cy5 dye) | ssDNA-21 (Cy5.5 dye) |
| Multiplexed ssDNA assays in buffer | Cy3.5 | 1 | 0.002 ± 0.001 | −0.006 ± 0.028 |
| | Cy5 | 0.954 ± 0.0393 | 1 | 0.019 ± 0.030 |
| | Cy5.5 | 0.349 ± 0.008 | 0.438 ± 0.007 | 1 |
| Multiplexed ssDNA assays in serum | Cy3.5 | 1 | 0.009 ± 0.002 | −0.072 ± 0.023 |
| | Cy5 | 1.136 ± 0.016 | 1 | −0.013 ± 0.046 |
| | Cy5.5 | 0.355 ± 0.002 | 0.421 ± 0.009 | 1 |

1.6 Homogeneous Multiplexed Micro-RNA and ssDNA Assays

All assays were performed on the KRYPTOR fluorescence plate reader by measuring time-gated acceptor intensities and applying the bio-spectral crosstalk correction. Total sample volumes (inside the micro wells) were always 150 μL.

microRNA and ssDNA Assay Calibration Curves in Buffer:

Buffer composition for the microRNA assays was 25 mM HEPES buffer, 50 mM NaCl, 2 mM $MgCl_2$, 0.4 mM ATP, 100 μg/ml single stranded salmon sperm DNA, pH7.4+0.1% BSA, RNA secure reagent treated. Buffer composition for the ssDNA assays was 25 mM HEPES buffer, 150 mM NaCl, 10 mM $MgCl_2$, 1 mM ATP, 100 μg/ml single stranded salmon sperm DNA, pH7.4+0.1% BSA. All three sensors for miRNA-20a, miRNA 20b, miRNA-21 were dissolved in the samples with concentrations of 9 nM P1, 3 nM P2a-F2, 3 nM P2b-F2, 3 nM P2c-F2, 6 nM A1-A3a, 3 nM A4a-A2a, 3 nM A4b-A2b, 3 nM A1-A3b, 3 nM A4c-A2c for the microRNA sensors and 9 nM F1-P1 (ssDNA), 3 nM P2a-F2, 3 nM P2b-F2, 3 nM P2c-F2, 6 nM A1-A3a, 3 nM A4a-A2a (ssDNA), 3 nM A4b-A2b (ssDNA), 3 nM A1-A3b (ssDNA and miRNA in serum), 3 nM A4c-A2c (ssDNA) for the ssDNA sensors. In the different assays for the calibration of each sensor (calibration curves) the concentration of one target was varied from 0 to 750 pM while the other two targets were a) both not present, b) and c) one not present and the other one at a constant concentration of 750 pM, or d) both present at a constant concentration of 750 pM. For statistical analysis of microRNA assays, all samples were prepared and measured once (50 laser pulses per target, which corresponds to 2.5 s per target or 7.5 s per sample). For statistical analysis of ssDNA assays, all samples were prepared three times and measured once (100 laser pulses per target, which corresponds to 5 s per target or 15 s per sample). For determination of the zero-concentration standard deviation (for LOD calculation) additional 10 zero-concentration (of the target to be calibrated) samples of each assay were prepared and measured once. All samples were incubated for 2 hrs at 37° C. prior to the measurements.

microRNA and ssDNA Assays with Varying Target Concentrations:

Buffer composition and sensor concentrations were the same as for the target calibration assays (vide supra). For both microRNA and ssDNA nine samples with varying target concentrations between 50 and 500 pM were prepared. For microRNA, all samples were prepared and measured once (50 laser pulses per target, which corresponds to 2.5 s per target or 7.5 s per sample). Error bars were determined by the deviations in the crosstalk correction matrices (Tables 3 and 4). For ssDNA, all samples were prepared three times and measured once (100 laser pulses per target, which corresponds to 5 s per target or 15 s per sample). All samples were incubated for 2 hrs at 37° C. prior to the measurements.

microRNA and ssDNA Assay Calibration Curves in Serum:

Buffer composition for the microRNA assays was 25 mM HEPES buffer, 50 mM NaCl, 10 mM $MgCl_2$, 0.4 mM ATP, 100 μg/ml single stranded salmon sperm DNA, pH 7.4+ 0.1% BSA, containing 5% of new born calf serum. Serum-containing buffer was treated with RNA secure reagent to inactivate RNase activity before addition of targets or sensors. Buffer composition for the ssDNA assays was 25 mM HEPES buffer, 150 mM NaCl, 10 mM $MgCl_2$, 1 mM ATP, 100 μg/ml single stranded salmon sperm DNA, pH 7.4+ 0.1% BSA, containing 5% of new born calf serum, Serum-containing buffer was heated to inactivate DNase activity. All three sensors were dissolved in the samples with concentrations of 9 nM P1, 3 nM P2a-F2, 3 nM P2b-F2, 3 nM P2c-F2, 6 nM A1-A3a (ssDNA and miRNA in serum), 3 nM A4a-A2a, 3 nM A4b-A2b, 3 nM A1-A3b, 3 nM A4c-A2c for the microRNA determination and 9 nM F1-P1 (ssDNA), 3 nM P2a-F2, 3 nM P2b-F2, 3 nM P2c-F2, 6 nM A1-A3a, 3 nM A4a-A2a (ssDNA), 3 nM A4b-A2b (ssDNA), 3 nM A1-A3b (ssDNA and miRNA in serum), 3 nM A4c-A2c (ssDNA) for the ssDNA determination. The 150 μL total assay volume was composed of 142.5 μL buffer and 7.5 μL serum that contained the different targets. In the different assays for the calibration of each sensor (calibration curves) the concentration of one target was varied from 0 to 750 pM (concentrations in the complete assay volume corresponds to 0 to 15 nM in the serum) while the other two targets were both not present. For all statistical analysis each sample was prepared three times and measured once (100 laser pulses per target, which corresponds to 5 s per target or 15 s per sample). For determination of the zero-concentration standard deviation (for LOD calculation) additional 10 zero-concentration (of the target to be calibrated) samples of assays, in which the other two targets were a) both not present, b) and c) one not present and the other one at a constant concentration of 750 pM, or d) both present at a constant concentration of 750 pM, were prepared 10 times and measured once. For LOD calculation the calibration curves of the assays b to c were considered to be equal to the one from assay a. All samples were incubated for 2 hrs at 37° C. prior to the measurements.

2. Results

2.1 Photophysical Properties

Figure 2B:
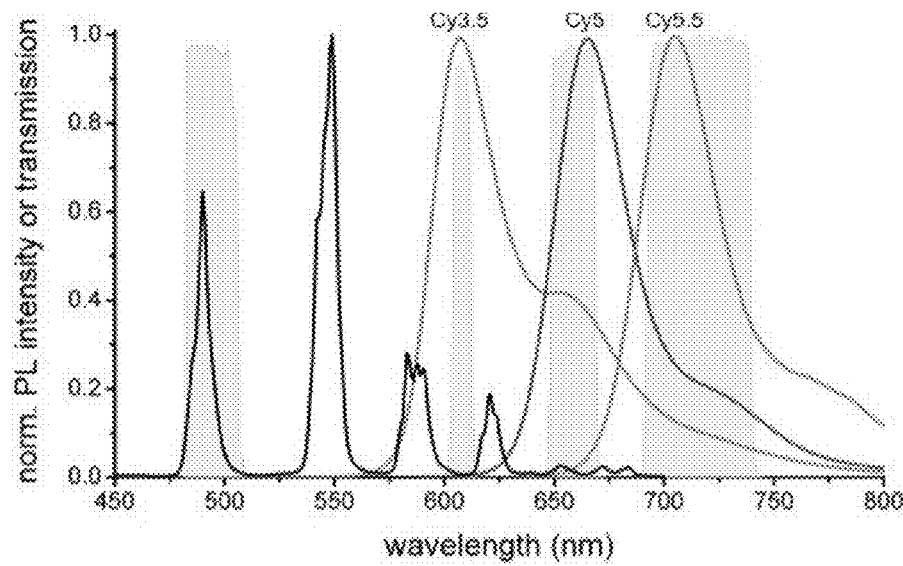
Figure 2C:
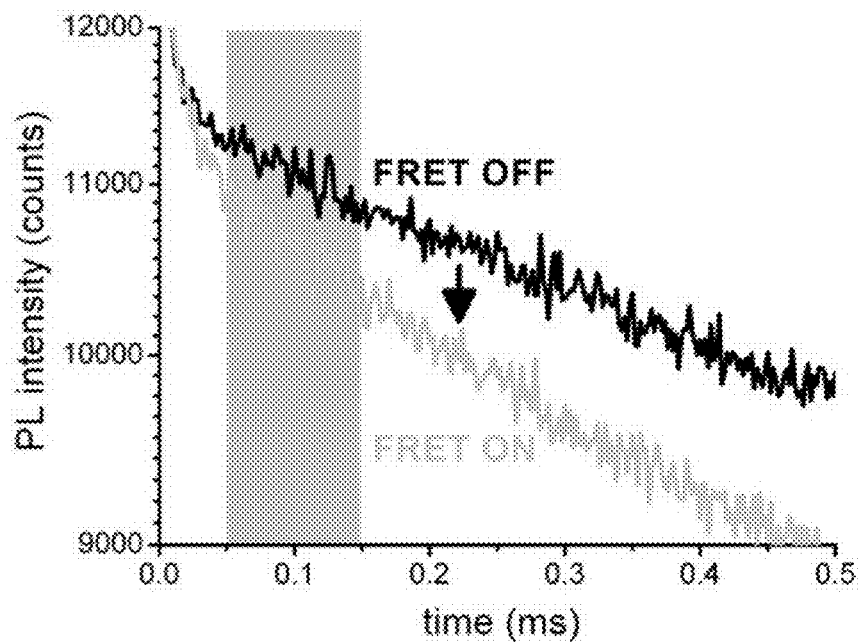
Figure 2D:
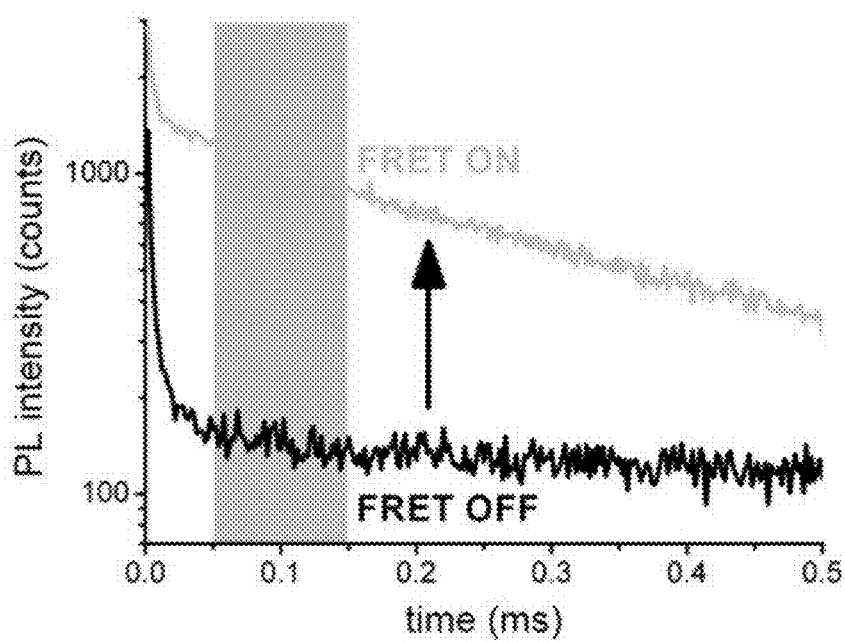

The FRET process for a specific quantification of different nucleic acid targets uses a Lumi4-Tb FRET-donor (Tb) and three different organic dye acceptors (Cy3.5, Cy5 and Cy5.5). Absorption and photoluminescence (PL) spectra are shown in FIGS. 2a and b. Tb can be efficiently excited in the UV (337 nm), which leads to mainly four bright and narrow PL emission bands in the 475 nm to 640 nm wavelength range. This emission spectrum overlaps with the absorbance spectra of the three different dyes, thus allowing FRET from Tb to all three dyes. Apart from the one-donor-multiple-acceptors configuration, the extremely long excited-state lifetime of the Tb (~2.7 ms) is another large advantage for multiplexed biosensing. This long-lived PL can be used for time-gated PL detection as shown in FIG. 2c (for Tb-donor PL) and 2d (for dye-acceptor PL), which efficiently suppresses all background-fluorescence, thus leading to highly sensitive detection. In the case of separated Tb-donor and dye-acceptors (FIG. 1a) only long-lifetime PL from the Tb can be detected ("FRET off"). The PL signal is strong in the Tb detection channel (bandpass wavelength for the detection channels are shown in FIG. 2b) and relatively weak in the dye acceptor detection channels (spectral crosstalk from the Tb donor PL). Upon the formation of stable sensor-microRNA double-strands (FIGS. 1c and 1d), Tb-donor and dye-acceptors are in close proximity and FRET can occur ("FRET on"). This energy transfer will lead to Tb-donor quenching and very efficient dye-acceptor sensitization. Using the flexible kit according to the invention, the donor-acceptor distances have been optimized for an optimum signal change (even at very low target concentrations) in the time-window from 0.05 to 0.15 ms (gray background in FIGS. 2c and 2d).

2.2 Selectivity for Different RNA or DNA Sequences

To demonstrate the performance of the kit of the invention in distinguishing even very similar RNA or DNA sequences, the Inventors selected the three microRNA targets hsa-miR-20a-5p (miRNA-20a, 23 nucleotides), hsa-miR-20b-5p (miRNA-20b, 23 nucleotides) and hsa-miR-21-5p (miRNA-21, 22 nucleotides) as well as their ssDNA analogues (ssDNA-20a/20b/21). The flexible kit design (FIGS. 1a to 1e) allowed the use of a universal Tb-donor probe oligo. Because the dye-acceptor probe oligos (using the dyes Cy3.5, Cy5 and Cy5.5) are specific for the three different targets, the microRNA FRET sensors for miRNA-20a, miRNA-20b and miRNA-21 are named respectively "Tb-miRNA-20a-Cy3.5", "Tb-miRNA-20b-Cy5" and "Tb-miRNA-21-Cy5.5" (FIG. 1d). All adaptor oligos share the same PRB-D sequence. Due to the target similarity the sensors Tb-miRNA-20a-Cy3.5 and Tb-miRNA-20b-Cy5 also share the same TGT-D sequence. All other sensor sequences are adapted to the respective targets (FIGS. 1d and 1e). The major challenge concerning selectivity is the distinction between miRNA-20a and 20b, whose difference in the RNA sequence can be found in only two out of 23 nucleotides (1 and 10—from 5' to 3'—are uracil for miRNA-20a and cytosine for miRNA-20b—see Table 1). The differences in base pairing with the adaptor oligos are illustrated in FIG. 1e. Such strong sequence homologies are especially difficult to distinguish for homogeneous assays, which do not contain any separation, washing or amplification steps. In order to find the optimum ligation conditions for selectivity, the Inventors performed Tb-miRNA-20a-Cy3.5 and Tb-miRNA-20b-Cy5 single sensor assays with both targets and different ligase concentrations. The simultaneous dye-acceptor and Tb-donor measurement helps to perform a ratiometric assay using the FRET-ratio as the assay detection signal:

$$FRET-\text{ratio} = \frac{\text{dye} - PL(0.05 - 0.15 \text{ ms})}{Tb - PL(0.05 - 0.15 \text{ ms})} \quad (1)$$

where dye-PL (0.05-0.15 ms) and Tb-PL (0.05-0.15 ms) are the respective PL intensities of the dye-acceptors and the Tb-donor in the detection window from 0.05 to 0.15 ms after pulsed laser excitation. The results (FIGS. 3a and 3b) reveal differences in both selectivity and optimum ligase concentration. The Tb-miRNA-20a-Cy3.5 sensor shows increasing FRET-ratios for the matching miRNA-20a with increasing ligase concentrations up to 0.1 CEU, whereas the FRET-ratios for the mismatched miRNA-20b are equal to the background FRET-ratio (no target). Higher ligase concentrations mainly increase the FRET-signal of the mismatched sample and are therefore not suitable for highly selective detection. The Tb-miRNA-20b-Cy5 sensor is much less dependent on ligase concentration. At optimal conditions of 0.1 CEU ligase, both kits show the highest match-to-mismatch ratios. These values (7.1 vs. 2.9) also reflect the significantly higher selectivity of the miRNA-20a sensor. The inventors also performed these experiments for the ssDNA analogues (FIGS. 6a to 6d), which resulted in an optimal DNA-ligase concentration of 2 CEU. In order to verify the sensor selectivity against other nucleic acid sequences with strong homology, the Inventors tested both sensors for ssDNA using five additional ssDNA targets with very similar sequences (cf. Table 1) to ssDNA-20a and ssDNA-20b. All mismatched ssDNA targets show FRET-ratios equal to the background FRET-ratio (no target), whereas the matched targets lead to a significant increase of the FRET-ratio (FIGS. 6a to 6d).

2.3 Multiplexing and Bio-Spectral Crosstalk Correction

Apart from a highly sensitive and selective homogenous nucleic acid assay, one of the main goals of the study was the multiplexed detection of several microRNAs or ssDNAs from a single low-volume sample. In order to demonstrate this, the Inventors designed a kit for triplexed assays of the three different microRNAs miRNA-20a, miRNA-20b and miRNA-21 (FIG. 1d) or their ssDNA analogues, performed on a clinical fluorescence immunoassay plate reader (KRYPTOR). The detection of the Tb-donor and the three dye-acceptors from a single sample is very challenging because there is significant spectral crosstalk from the Tb-PL into the dye detection channels as well as between the different dye channels (FIG. 2b). In order to overcome this problem the Inventors used the recently developed spectral crosstalk correction (Geißler et al., 2013). This method uses a matrix, which includes all possible crosstalks from the different fluorophores in the different detection channels. This matrix is multiplied with the PL intensities measured in each detection channel to efficiently correct for the significant spectral crosstalk. In contrast to the pure spectral crosstalk the strong sequence homology of the selected targets (miRNA-20a and miRNA-20b) in combination with a fixed buffer composition and a constant working temperature for all three sensors within a single sample also generated biological crosstalk. In the triplexed assay, this biological crosstalk is mainly characterized by binding of miRNA-20a targets to the Tb-miRNA-20b-Cy5 sensor due to the strong similarity in the sequences of the two targets 20a and 20b. Due to the interaction of biological and spectral interferences, the correction method used in the present invention is named crosstalk correction. For the generation of bio-spectral crosstalk correction matrices the Inventors used all three sensors within one sample. For each target (three mixtures of single target with triple sensors) the fraction of bio-spectral crosstalk of Tb and dyes (normalized to the signal intensities in their dedicated detection channels) to the non-corresponding detection channels was measured. The results of spectral crosstalk between Tb and different dye channels are illustrated in Table 2. The results of bio-spectral crosstalk of multiplexed sensors for microRNA or ssDNA are respectively illustrated in Table 3 and Table 4.

2.4 Homogeneous Multiplexed microRNA and ssDNA Assays

Figure 4A:
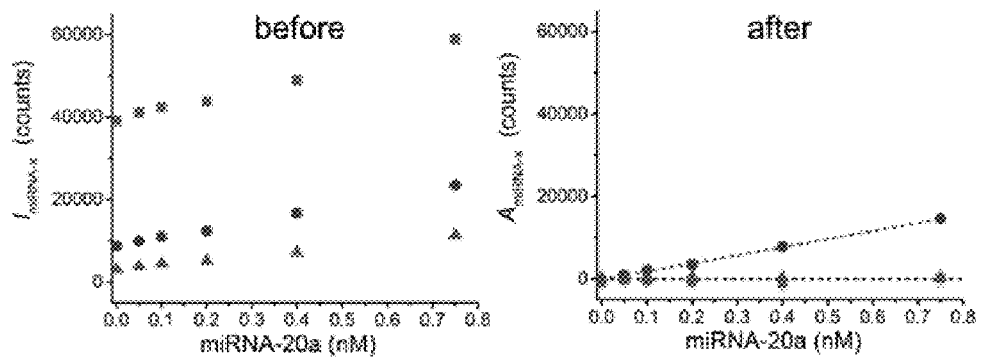
FIGS. 4a to 4c show multiplexed microRNA assays.
Figure 4B:
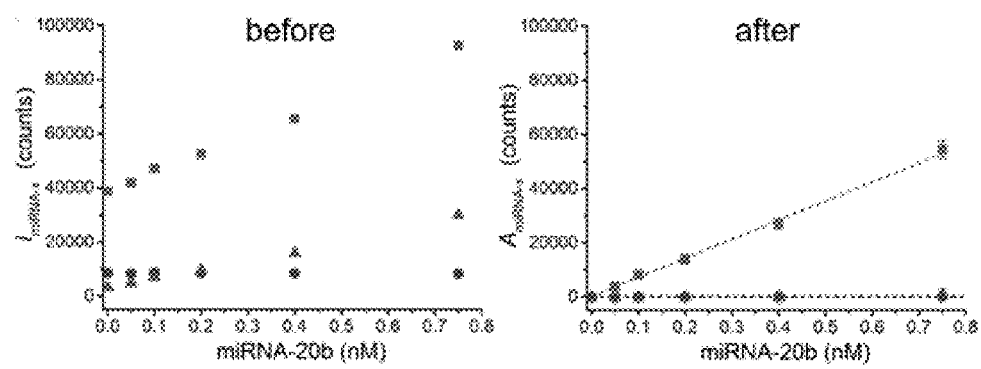
Figure 4C:
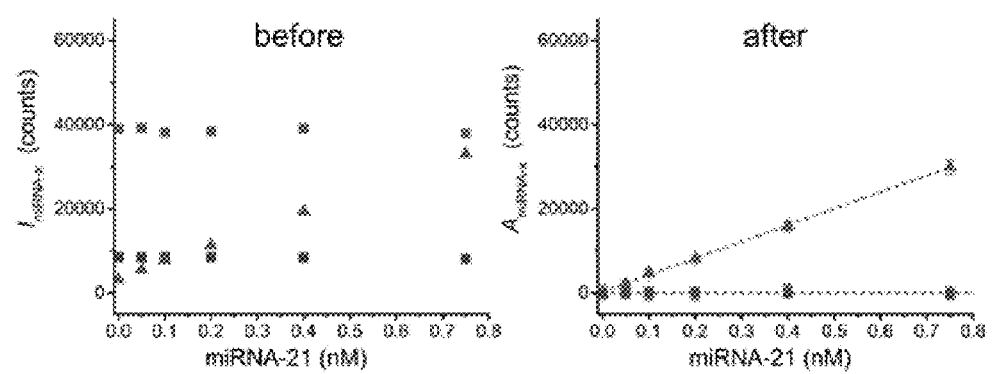
Figure 5A:
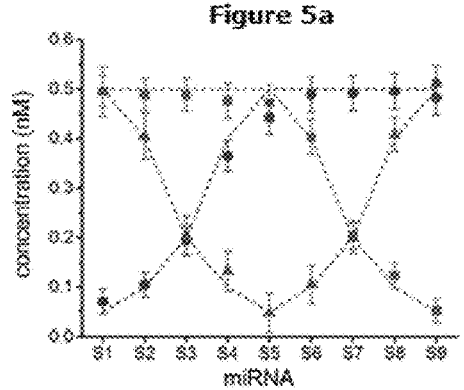
FIGS. 5a to 5d show multiplexed detection of varying microRNA concentrations and microRNA detection directly in serum. Squares correspond to the signals obtained by sensor Tb-miRNA-20b-Cy5. Circles correspond to the signals obtained by sensor Tb-miRNA-20a-Cy3.5. Triangles correspond to the signal obtained by sensor Tb-miRNA-21-Cy5.5.
Figure 7A:
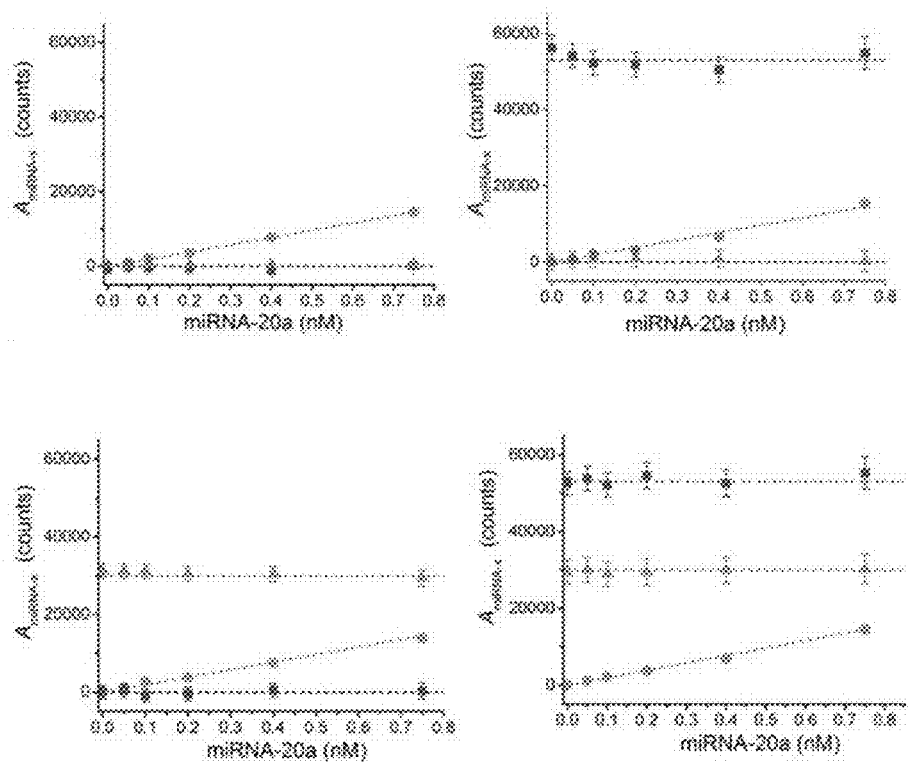
FIGS. 7a to 7c show multiplexed microRNA assay calibration curves after bio-spectral crosstalk correction for the targets miRNA-20a (FIG. 7a), miRNA-20b (FIG. 7b) and miRNA-21 (FIG. 7c). The abscissa corresponds to the concentration of nucleic acid target in the sample. Squares correspond to the signals obtained by sensor Tb-miRNA-20b-Cy5. Circles correspond to the signals obtained by sensor Tb-miRNA-20a-Cy3.5. Triangles correspond to the signals obtained by sensor Tb-miRNA-21-Cy5.5. The calibration curves show the target-specific signal intensities over increasing target concentrations. All assays contain all three sensors and one target with increasing concentration. The other two targets are not present in the sample (left graphs) or have a concentration of 750 pM for one of the targets (both middle graphs), or both targets (right graphs). Even the presence of both other targets at high concentrations does not significantly change the calibration curves and also the constant concentrations of these two other targets can be precisely determined.
Figure 7B:
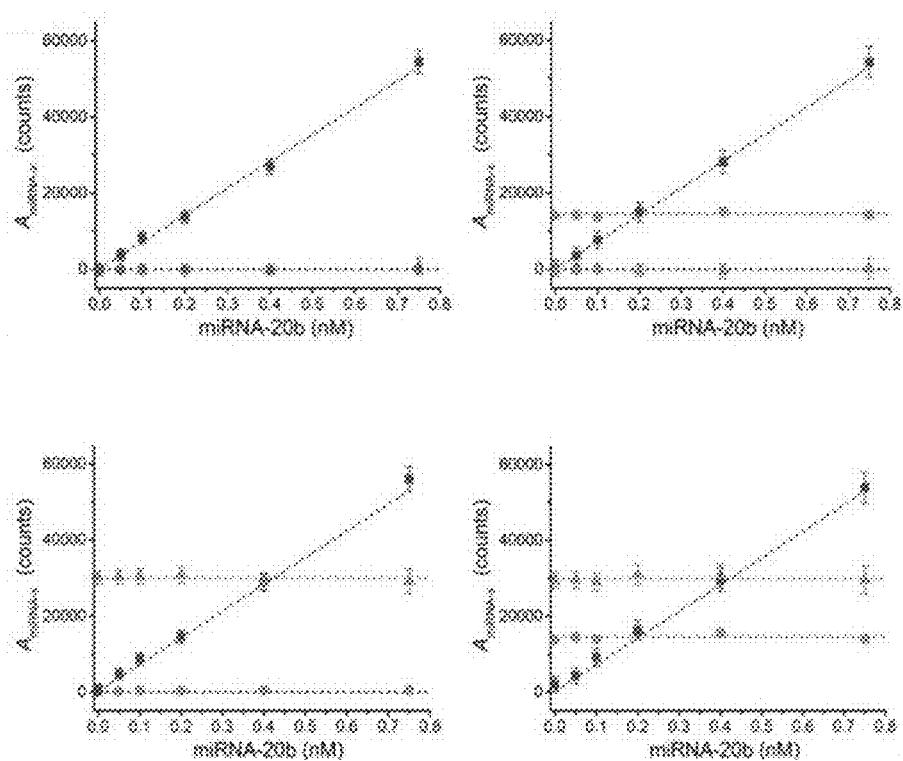
Figure 7C:
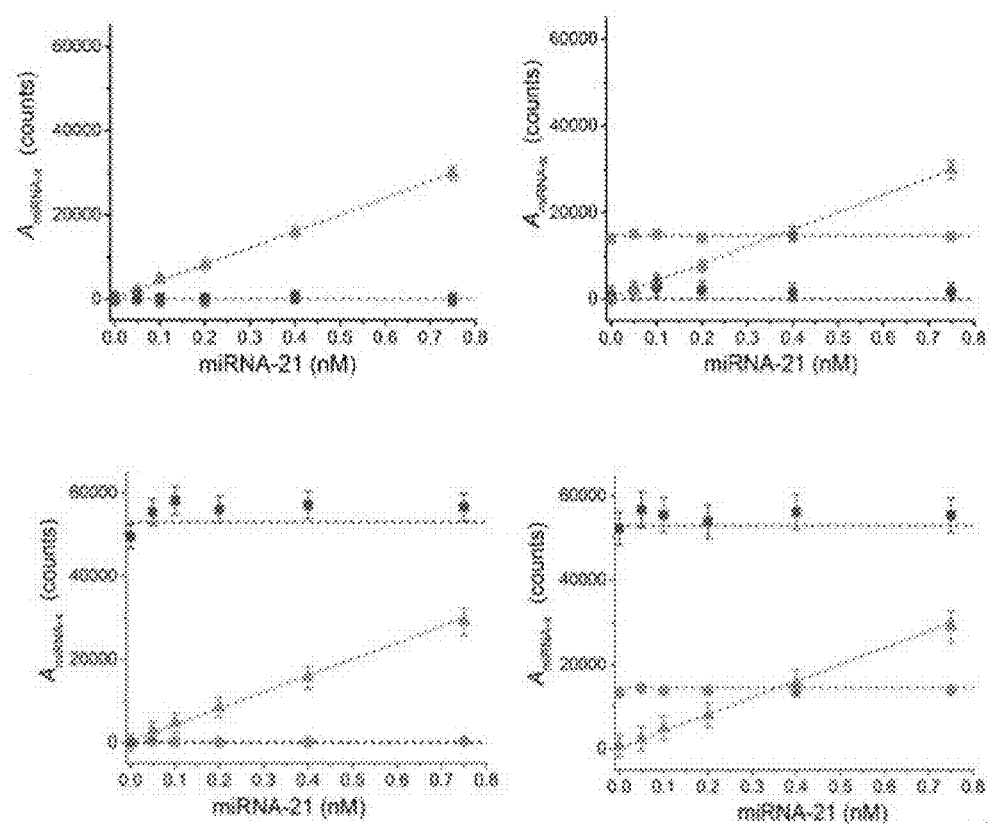
Figure 8A:
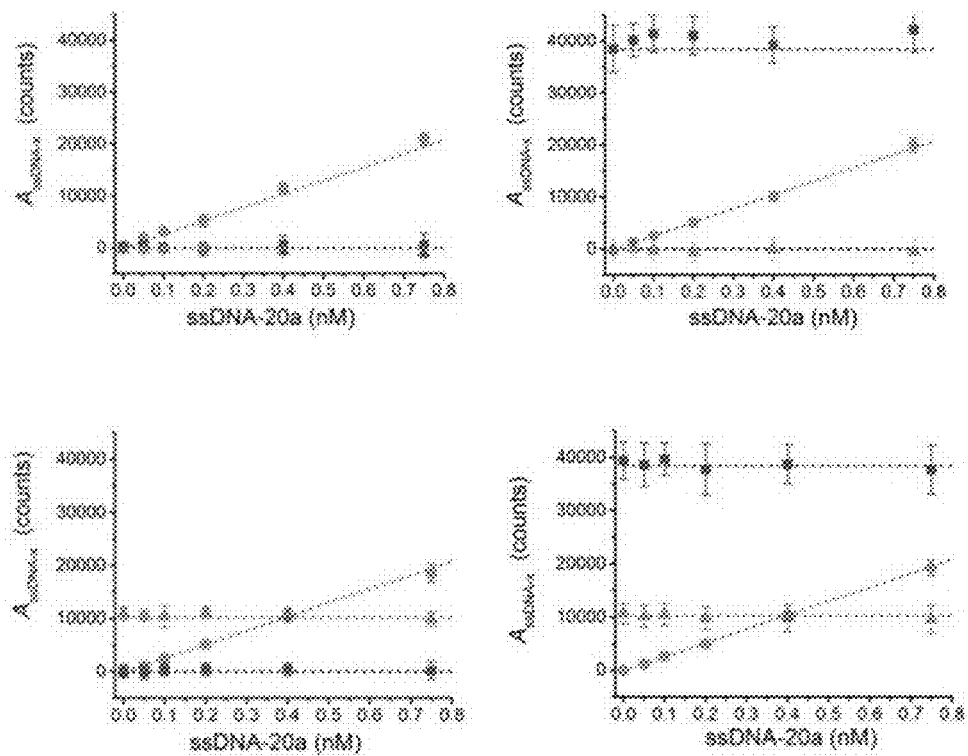
FIGS. 8a to 8c show multiplexed ssDNA assay calibration curves after bio-spectral crosstalk correction for the targets ssDNA-20a (FIG. 8a), ssDNA-20b (FIG. 8b) and ssDNA-21 (FIG. 8c). The abscissa corresponds to the concentration of nucleic acid target in the sample. Squares correspond to the signals obtained by sensor Tb-ssDNA-20b-Cy5. Circles correspond to the signals obtained by sensor Tb-ddDNA-20a-Cy3.5. Triangles correspond to the signals obtained by sensor Tb-ssDNA-21-Cy5.5. The calibration curves show the target-specific signal intensities over increasing target concentrations. All assays contain all three sensors and one target with increasing concentration. The other two targets are not present in the sample (left graphs) or have a concentration of 750 pM for one of the targets (both middle graphs), or both targets (right graphs). Even the presence of both other targets at high concentrations does not significantly change the calibration curves and also the constant concentrations of these two other targets can be precisely determined.
Figure 8B:
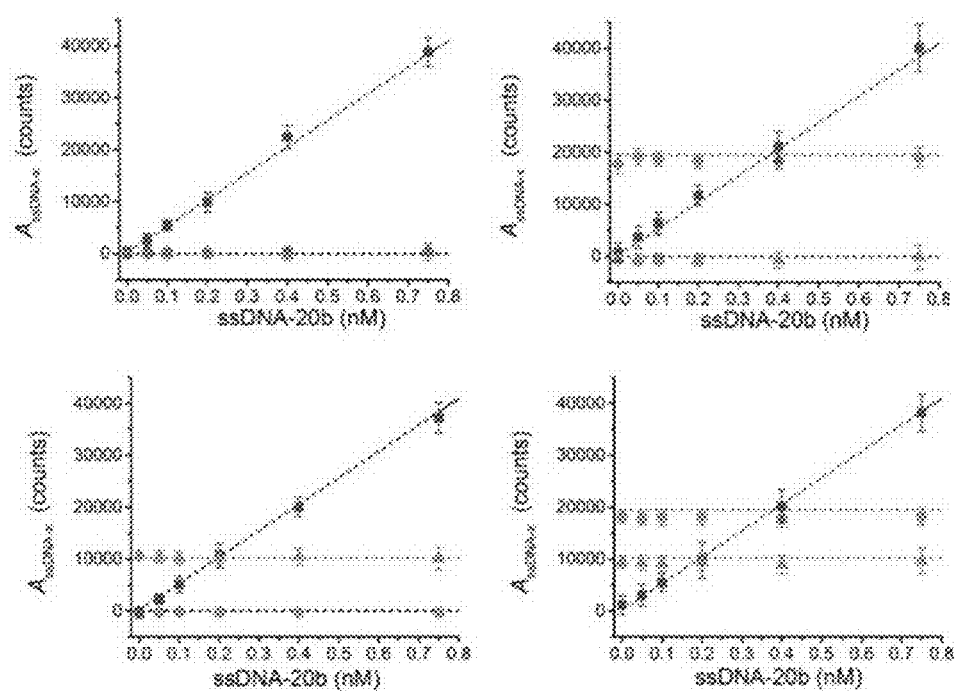
Figure 8C:
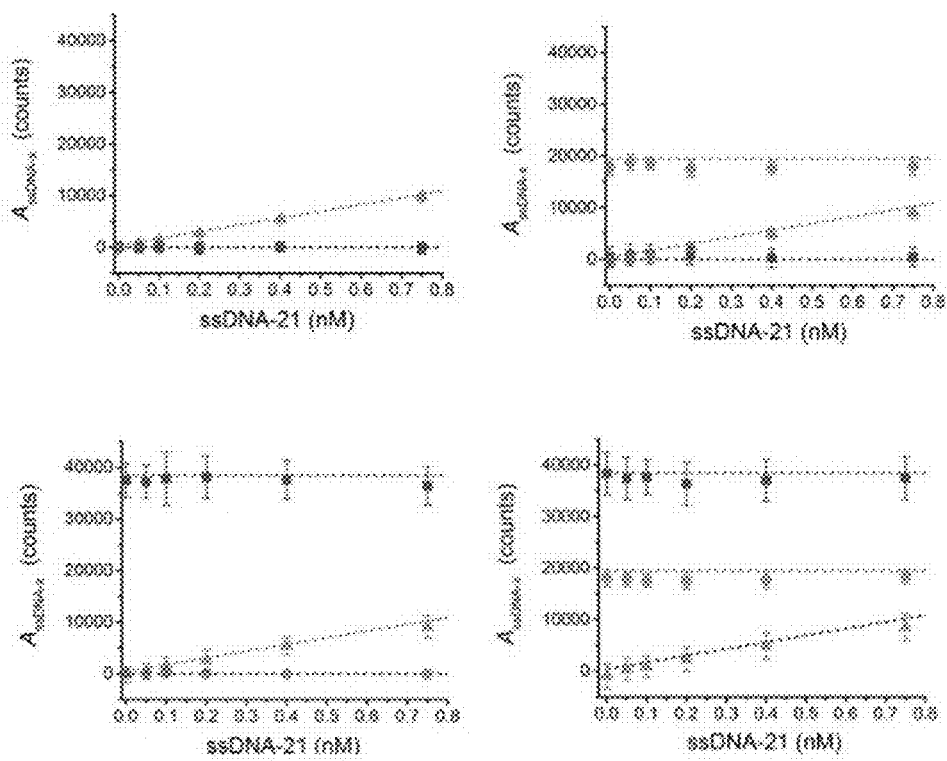
Figure 9A:
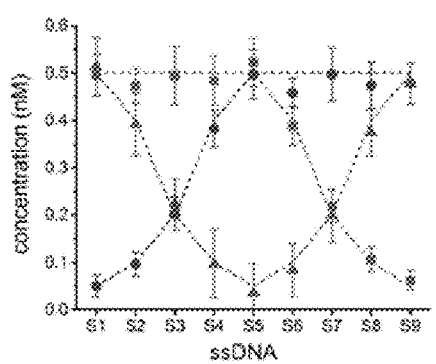
FIGS. 9a to 9d illustrate multiplexed detection of varying ssDNA concentrations and ssDNA detection directly in serum.
Figure 9B:
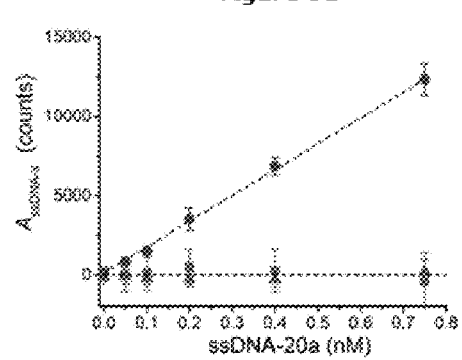
Figure 9C:
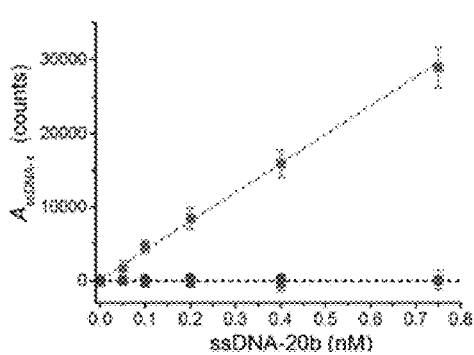
Figure 9D:
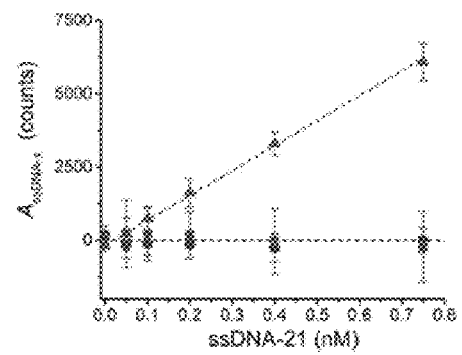

FIGS. 4a to 4c show calibration curves of the multiplexed microRNA assays for three different targets without and with bio-spectral crosstalk correction. The strong difference in uncorrected ($I_{miRNA-x}$) and corrected ($A_{miRNA-x}$) time-gated PL intensity values demonstrates the necessity as well as the efficiency of the combined correction method, which allows a precise calibration of $A_{miRNA-x}$ to the target concentration. In order to verify the bio-spectral crosstalk correction method for microRNA and ssDNA assays under more realistic conditions the Inventors also measured the calibration curves of the three different targets when the other two targets were present at high and low, low and high or high and high concentrations (these nine additional assays each for microRNA and ssDNA are shown in FIGS. 7 and 8). For a more condensed presentation of the ability to precisely measure very low concentrations of the three targets at different concentrations, the Inventors prepared nine samples with varying target concentrations between 50 and 500 pM and measured these with the method of the invention using the calibration curves from FIGS. 4a to 4c. The results (FIG. 5a for microRNA and FIG. 9a for ssDNA)

provide an impressive demonstration of the extremely high specificity and sensitivity of the method of the invention for detecting microRNA and ssDNA, even when all three targets are present in the same sample at varying concentrations.

Figure 5B:
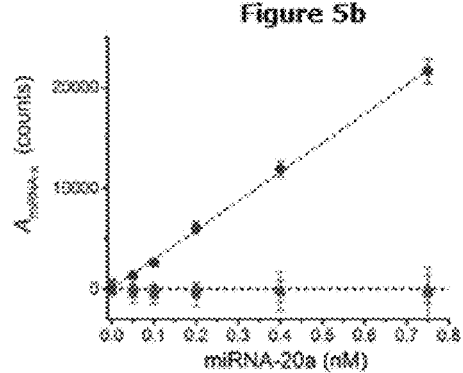
Figure 5C:
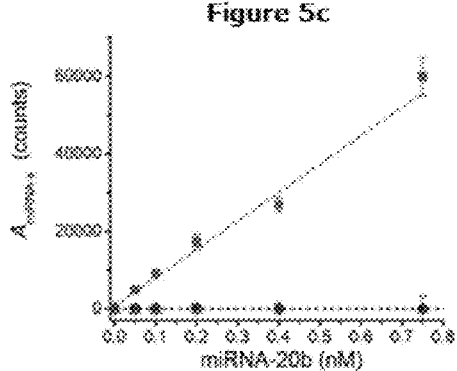
Figure 5D:
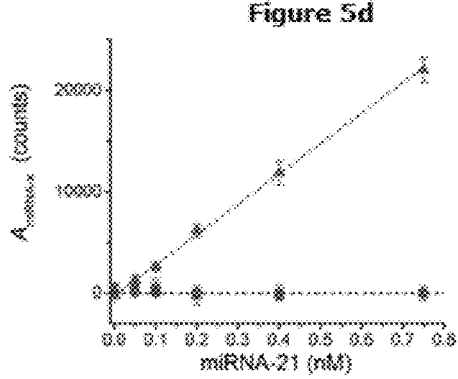
Figure 6A:
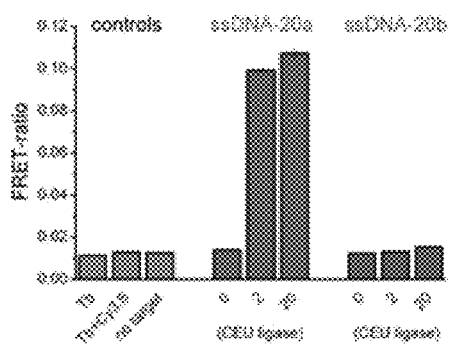
FIGS. 6a to 6d show the selectivity of sensors for ssDNA targets.
Figure 6B:
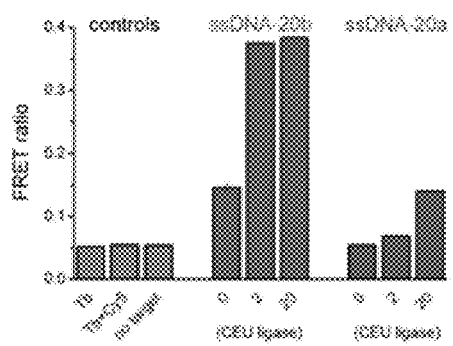
Figure 6C:
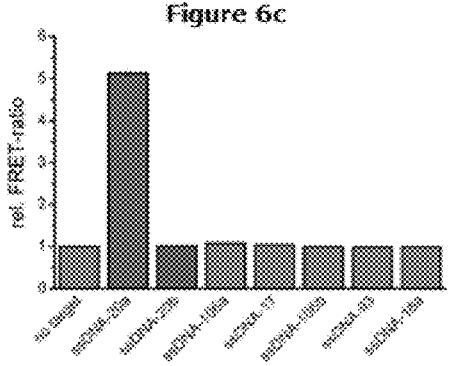
Figure 6D:
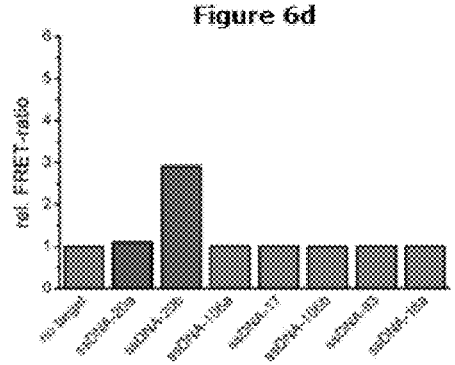

To go even one step further than the clinical scenario of measuring microRNA from blood or tissue extracts the assay of the invention are tested with direct microRNA detection in a few-microliters of serum (proof-of-principle for POCT). Due to high levels of plasma nuclease activity, which quickly degrades exogenously added microRNAs (in contrast to the extremely stable endogenous microRNAs), the Inventors used nuclease-inactivated samples containing 5% of serum (corresponding to 7.5 µL inside the 150 µL sample volume). FIGS. 5b-d show the excellent performance of the assays for the detection of the three different targets. It should be noted that the experimental conditions had to be slightly changed in order to perform these measurements (A3b in FIG. 1d was DNA and $Mg^{2+}$ concentration was 10 mM instead of 2 mM). These conditions offered higher signal intensities compared to the buffer measurements. The serum-based assays demonstrate the feasibility of a direct homogeneous multiplexed microRNA and ssDNA detection directly in serum.

For the determination of the limits of detection (LOD, zero-concentration value plus three times its standard deviation) of the buffer and serum-based assays under the different conditions (with and without the other targets present is in the samples) the Inventors used the various calibration curves and calculated the standard deviation of the $A_{miRNA-x}$ values of 10 zero-concentration samples. The results are illustrated in Table 5.

TABLE 5

Limits of detection (LODs) of the different microRNA targets and ssDNA targets 20a, 20b and 21 in 150 µL buffer and 7.5 µL serum samples under different sample conditions (with and without the presence of other targets in the sample).

| conditions* | Target | | | | | |
|---|---|---|---|---|---|---|
| | miRNA-20a | miRNA-20b | miRNA21 | ssDNA-20a | ssDNA-20b | ssDNA-21 |
| | LOD in 150 µL buffer-based sample (in pM) | | | | | |
| X | 23 | 23 | 21 | 11 | 17 | 25 |
| X + (750 pM Y) | 37 | 29 | 29 | 19 | 29 | 57 |
| X + (750 pM Z) | 36 | 29 | 27 | 15 | 21 | 40 |
| X + (750 pM Y and Z) | 31 | 17 | 23 | 15 | 27 | 86 |
| average | 32 | 24 | 25 | 15 | 23 | 52 |
| | LOD in 7.5 µL serum (in pM) | | | | | |
| X | 230 | 210 | 250 | 390 | 460 | 610 |
| X + (750 pM Y) | 150 | 250 | 700 | 420 | 450 | 1900 |
| X + (750 pM Z) | 210 | 1070 | 740 | 400 | 810 | 1720 |
| X + (750 pM Y and Z) | 200 | 410 | 1840 | 470 | 490 | 3680 |
| average | 200 | 490 | 880 | 420 | 550 | 1980 |

*if X = 20a then Y = 20b and Z = 21; if X = 20b then Y = 21 and Z = 20a; if X = 21 then Y = 20b and Z = 20a The results in Table 5 demonstrate the very low detection limits (below 40 pM for microRNA and below 90 pM for ssDNA) of the multiplexed assays in buffer. They also show the drawbacks of using only a few microliters of serum and of reduced selectivity for the serum-based assays (significantly higher LODs when all targets are present in the samples). Nevertheless, the LODs are still sub-nanomolar and demonstrate the feasibility of using the multiplexed assays of the invention also for direct POCT on microliter serum samples.

REFERENCES 1. de Planell-Saguer, M. & Rodicio, M. C. Analytical aspects of microRNA in diagnostics: a review. *Anal. Chim. Acta* 699, 134-152 (2011).
2. Gao, Z., Deng, H., Shen, W. & Ren, Y. A label-free biosensor for electrochemical detection of femtomolar microRNAs. *Anal. Chem.* 85, 1624-1630 (2013).
3. Abell, J. L., Garren, J. M., Driskell, J. D., Tripp, R. A. & Zhao, Y. Label-Free Detection of Micro-RNA Hybridization Using Surface-Enhanced Raman Spectroscopy and Least-Squares Analysis. *J. Am. Chem. Soc.* 134, 12889-12892 (2012).
4. Šípová, H. et al. Surface plasmon resonance biosensor for rapid label-free detection of microribonucleic acid at subfemtomole level. *Anal. Chem.* 82, 10110-10115 (2010).
5. Le, N.C. et al. Ultrathin and smooth poly(methyl methacrylate) (PMMA) films for label-free biomolecule detection with total internal reflection ellipsometry (TIRE). *Biosens. Bioelectron.* 36, 250-256 (2012).
6. Chen, S.-H. et al. A method of layer-by-layer gold nanoparticle hybridization in a quartz crystal microbalance DNA sensing system used to detect dengue virus. *Nanotechnology* 20, 215501 (2009).
7. Zhang, G.-J., Chua, J. H., Chee, R.-E., Agarwal, A. & Wong, S. M. Label-free direct detection of MiRNAs with silicon nanowire biosensors. *Biosen. Bioelectron.* 24, 2504-2508 (2009).
8. Jain, T., Guerrero, R. J., Aguilar, C. A. & Karnik, R. Integration of solid-state nanopores in microfluidic networks via transfer printing of suspended membranes. *Anal. Chem.* 85, 3871-3878 (2013).
9. Kulkarni, M. M. Digital multiplexed gene expression analysis using the nanostring Counter system. Current Protocols in Molecular Biology, Online ISBN: 9780471142720. John Wiley & Sons, Hoboken, N.J., USA. (2001).
10. Geißler, D., Stufler, S., Löhmannsröben, H. G. & Hildebrandt, N. Six-color time-resolved förster resonance energy transfer for ultrasensitive multiplexed biosensing. *J. Am. Chem. Soc.* 135, 1102-1109 (2013).

11. Fu et al., Semiconductor Quantum Rods as Single Molecule Fluorescent Biological Labels. *Nano Lett.* 2007; 7(1):179-82.
12. Hildebrandt, N. How to Apply FRET: Freom Experimental Design to Data Analysis. In: (I. Medintz, N. Hildebrandt, eds.) FRET—Förster Resonance Enery Transfer. From Theory to Applications. Wiley-VCH, ISBN 978-3-527-32816-1 (2014).
13. Hazer, B., Medintz, B. I., & Hildebrandt, N. Fluorescence in Nanobiotechnology: Sophisticated Fluorophores for Novel Applications, *Small* 8, No, 15, 2297-2326 (2012).

The invention claimed is:

1. A kit for detecting or quantifying the amount of one or multiple nucleic acid targets of 10-40 nucleotides, in a sample obtained from biological fluid, from an in vitro cell culture, from a tissue, from plants, from yeast, from bacteria or from exosomes, constituted by:
  (i) one universal energy donor probe, constituted by:
    an oligonucleotide named Nd-D of 5-100 nucleotides, and
    optionally, an overhang oligonucleotide named F1 of 1-50, nucleotides;
    said oligonucleotide Nd-D, when the oligonucleotide F1 is not present in said universal energy donor probe, or said oligonucleotide F1 when it is present in said energy donor probe, being labelled by a luminescent material with an excited-state lifetime of more than 50 ns as energy donor;
  (ii) at least one universal energy acceptor probe, each one being constituted by:

an oligonucleotide named Nd-A of 5-100 nucleotides, and optionally, an overhang oligonucleotide named F2 of 1-50, nucleotides;

said oligonucleotide Nd-A, when the oligonucleotide F2 is not present in said universal energy acceptor probe, or said oligonucleotide F2 when it is present in said universal energy acceptor probe, being labelled by a luminescent material as energy acceptor, said oligonucleotide Nd-A and said luminescent material being exclusive for each said universal energy acceptor probe;

(iii) at least one couple of two adaptors, the number of couples of two adapters being equal to that of universal energy acceptor probes, each couple of two adaptors being complementary to one unique nucleic acid target in said sample, one unique universal energy acceptor probe and the universal energy donor probe, each couple of adaptors being constituted by:

(a) a first adaptor, which is an oligonucleotide comprising:

a fragment named PRB-D of at least 5 nucleotides whose sequence is completely complementary to that or a part of oligonucleotide Nd-D; and a fragment named TGT-D of at least 3 nucleotides, whose sequence is completely complementary to that of a first part of said nucleic acid target, said first part being situated at 3' or 5' end of said nucleic acid target; and (b) a second adaptor, which is an oligonucleotide comprising:

a fragment named PRB-A of at least 5 nucleotides whose sequence is completely complementary to that or a part of oligonucleotide Nd-A, and a fragment named TGT-A of at least 3 nucleotides, whose sequence is completely complementary to that of a second part of said nucleic acid target, said second part being situated at another end of said nucleic acid target, each extremity of second part of said nucleic acid target being situated outside of aforementioned first part of said nucleic acid target;

(iv) optionally, a ligase and a polymerase; and (v) optionally, a reaction buffer.

2. The kit according to claim 1, wherein the nucleic acid target is chosen from a microRNA, a siRNA, a ssDNA or a mixture thereof.

3. The kit according to claim 1, wherein the biological fluid is chosen from serum, inactivated serum, plasma, or blood.

4. The kit according to claim 1, wherein the sample of a tissue is a sample obtained by biopsy or during surgical operation.

5. The kit according to claim 1, wherein the luminescent material with excited-state lifetime of more than 50 ns as an energy donor contains a lanthanide ion, or a transition metal, or a long-lifetime fluorophore, or a long-lifetime nanoparticle, or a combination thereof.

6. The kit according to claim 1, wherein the luminescent material as an energy acceptor is an organic fluorophore, or a non-fluorescent dark quencher, or a polymeric or dendrimeric dye, or a nanoparticle, or a naturally occurring fluorophore, or light harvesting complex, or a combination thereof.

7. The kit according to claim 1, wherein each couple of two adaptors is constituted by:

(a) a first adaptor, which is an oligonucleotide comprising:

a fragment PRB-D of at least 5 nucleotides whose sequence is completely complementary to that or a part of oligonucleotide Nd-D, and a fragment TGT-D of at least 3 nucleotides, whose sequence is at least completely complementary to that of a first part of said nucleic acid target, said first part being situated at 3' or 5' end of said nucleic acid target, and (b) a second adaptor, which is an oligonucleotide comprising:

a fragment PRB-A of at least 5 nucleotides whose sequence is completely complementary to that or a part of oligonucleotide Nd-A, and a fragment TGT-A of at least 3 nucleotides, whose sequence is at least completely complementary to that of the remaining part of said nucleic acid target.

8. The kit according to claim 1, for detecting and quantifying the amount of five single-strand nucleic acid targets of 10-40 nucleotides in a sample obtained from biological fluid, from an in vitro cell culture, from a tissue, from plants, from yeast, from bacteria or from exosomes, constituted by:

(i) one universal energy donor probe, constituted by:

an oligonucleotide Nd-D of 5-100 nucleotides, and optionally, an overhang oligonucleotide F1 of 1-50 nucleotides, said oligonucleotide Nd-D, when the oligonucleotide F1 is not present in said universal energy donor probe, or said oligonucleotide F1 when it is present in said universal energy donor probe, being labelled by a Tb complex as energy donor, (ii) five universal energy acceptor probes, each one being constituted by:

an oligonucleotide Nd-A of 5-100 nucleotides, and optionally, an overhang oligonucleotide F2 of 1-50 nucleotides, said oligonucleotide Nd-A, when the oligonucleotide F2 is not present in said universal energy acceptor probe, or said oligonucleotide F2 when it is present in said universal energy acceptor probe, being labelled by an organic fluorophore as energy acceptor, said oligonucleotide Nd-A and said organic fluorophore being exclusive for each said universal energy acceptor probe, (iii) five couples of two adaptors, each couple being complementary to one unique single-strand nucleic acid target in said sample, one unique universal energy acceptor probe and the universal energy donor probe, each couple of adaptors being constituted by:

(a) a first adaptor, which is an oligonucleotide constituted by:

a fragment PRB-D, whose sequence is completely complementary to that of oligonucleotide Nd-D, and a fragment TGT-D of at least 3 nucleotides, whose sequence is completely complementary to that of a first part of said single-strand nucleic acid target, said first part being situated at 5' or 3' end of said single-strand nucleic acid target, and (b) a second adaptor, which is an oligonucleotide constituted by:

a fragment PRB-A, whose sequence is completely complementary to that of oligonucleotide Nd-A, and a fragment TGT-A at least 3 nucleotides, whose sequence is completely complementary to that of the remaining part of said single-strand nucleic acid target, (iv) optionally, a ligase and a polymerase, and (v) optionally, a reaction buffer.

9. A method for detecting or quantifying the amount of one or multiple single-strand nucleic acid targets of 10 to 40 nucleotides, in a sample obtained from biological fluid, from an in vitro cell culture, from a tissue, from plants, from yeast, from bacteria or from exosomes, said method comprising the steps of:
  (i) adding to said sample or a solution extracted from said sample, the kit as defined in claim 1 and optionally a ligase and a polymerase and/or a reaction buffer, when the kit does not comprise said ligase and polymerase and/or said reaction buffer, to form a complex having stable double-strands;
  (ii) measuring photoluminescence emission intensities issued from a universal energy donor and different universal energy acceptors; and
  (iii) comparing photoluminescence emission intensities obtained in previous step with pre-established standard intensities to determine the amount of nucleic acid target.

10. The method according to claim 9, wherein step (i) is carried out at a temperature comprised from 10° C. to 80° C.

11. The method according to claim 9, wherein photoluminescence emission intensity of a universal energy donor and each universal energy acceptor are measured in a specific time window after light excitation.

12. The method according to claim 9, further comprising a step (ii'), which is between step (ii) and step (iii), of measuring biological and spectral crosstalk to calculate normalized photoluminescence emission intensities.

13. The method according to claim 9, wherein said single strand nucleic acid targets are microRNAs.

14. The method according to claim 9, wherein said method is used for in vitro diagnosis or prognosis of a disease.

15. The kit of claim 1 wherein the oligonucleotide named Nd-D has 10-40 nucleotides.

16. The kit of claim 1 wherein the overhang oligonucleotide named F1 has 1-10 nucleotides.

17. The kit of claim 1 wherein the oligonucleotide named Nd-A has 10-40 nucleotides.

18. The kit of claim 1 wherein the overhang oligonucleotide named F2 has 1-10 nucleotides.

19. The kit according to claim 5, wherein the luminescent material with excited-state lifetime of more than 50 ns as an energy donor contains the lanthanide ion selected from the group consisting of $Tb^{3+}$, $Eu^{3+}$, $Sm^{3+}$, $Dy^{3+}$, $Er^{3+}$, $Tm^{3+}$, or $Ho^{3+}$, or the transition metal selected from the group consisting of Ru, Ir, Os, Pt, or Re, or the long-lifetime fluorophore selected from the group consisting of fluorazaphores, or the long-lifetime nanoparticle selected from the group consisting of semiconductor quantum dots, or quantum rods, or a combination thereof.

20. The kit according to claim 1, wherein the luminescent material as an energy acceptor comprises the organic fluorophore selected from the group consisting of pyrene-, naphthalene-, coumarin-, fluorescein-, rhodamine- or cyanine-based dyes, or the nanoparticle selected from the group consisting of semiconductor quantum dot or quantum rod, or the naturally occurring fluorophore selected from the group consisting of fluorescent protein, or light harvesting complex, or a combination thereof.

* * * * *